United States Patent [19]
Buchanan et al.

[11] Patent Number: 5,900,322
[45] Date of Patent: *May 4, 1999

[54] ALIPHATIC-AROMATIC COPOLYESTERS AND CELLULOSE ESTER/POLYMER BLENDS

[75] Inventors: Charles M. Buchanan, Bluff City; Robert M. Gardner, Gray; Matthew D. Wood, Kingsport; Alan W. White, Kingsport; Steven C. Gedon, Kingsport; Fred D. Barlow, Jr., Kingsport, all of Tenn.

[73] Assignee: Eastman Chemical Company, Kingsport, Tenn.

[*] Notice: This patent is subject to a terminal disclaimer.

[21] Appl. No.: 08/763,562

[22] Filed: Dec. 10, 1996

Related U.S. Application Data

[60] Continuation of application No. 08/427,944, Apr. 26, 1995, Pat. No. 5,599,858, which is a division of application No. 08/163,441, Dec. 7, 1993, Pat. No. 5,446,079, which is a division of application No. 07/797,512, Nov. 21, 1991, Pat. No. 5,292,783, which is a continuation-in-part of application No. 07/736,262, Jul. 23, 1991, abandoned, which is a continuation-in-part of application No. 07/620,225, Nov. 30, 1990, abandoned.

[51] Int. Cl.$^6$ .......................... B32B 27/36; C08G 63/18
[52] U.S. Cl. ................... 428/480; 428/910; 528/301; 528/302; 528/308; 528/308.6; 528/308.7
[58] Field of Search ........................ 428/480, 910; 528/308, 308.6, 308.7, 301, 302

[56] References Cited

U.S. PATENT DOCUMENTS

| | | | |
|---|---|---|---|
| 1,683,347 | 9/1928 | Gray et al. | 536/72 |
| 1,698,049 | 1/1929 | Clarke et al. | 536/63 |
| 1,880,560 | 10/1932 | Webber et al. | 536/69 |
| 1,880,808 | 10/1932 | Clarke et al. | 536/63 |
| 1,984,147 | 12/1934 | Malm | 536/82 |
| 2,071,250 | 2/1937 | Carothers | 528/272 |
| 2,071,251 | 2/1937 | Carothers | 524/31 |
| 2,071,253 | 2/1937 | Carothers | 528/310 |
| 2,129,052 | 9/1938 | Fordyce | 106/196 |
| 3,602,225 | 8/1971 | Wielicki | 128/287 |
| 3,617,201 | 11/1971 | Beral et al. | 8/120 |
| 3,668,157 | 6/1972 | Combs et al. | 524/37 |
| 3,683,917 | 8/1972 | Comerford | 128/287 |
| 3,781,381 | 12/1973 | Koleske et al. | 524/44 |
| 3,922,239 | 11/1975 | Koleske et al. | 524/37 |
| 3,952,347 | 4/1976 | Comerford et al. | 5/335 |
| 4,328,059 | 5/1982 | Horlbeck et al. | 156/332 |
| 4,372,311 | 2/1983 | Potts | 128/287 |
| 4,401,805 | 8/1983 | Weemes et al. | 528/302 |
| 4,419,507 | 12/1983 | Sublett | 528/302 |
| 4,427,614 | 1/1984 | Barham et al. | 264/210.1 |
| 4,436,895 | 3/1984 | Barbee et al. | 528/288 |
| 4,503,098 | 3/1985 | Potts | 427/394 |
| 4,506,045 | 3/1985 | Waniczek et al. | 524/31 |
| 4,533,397 | 8/1985 | Wingler et al. | 106/181 |
| 4,749,773 | 6/1988 | Weaver et al. | 528/288 |
| 4,770,931 | 9/1988 | Pollock et al. | 428/304.4 |
| 4,826,493 | 5/1989 | Martini et al. | 604/327 |
| 4,826,903 | 5/1989 | Weaver et al. | 524/205 |
| 4,845,188 | 7/1989 | Weaver et al. | 528/272 |
| 4,880,592 | 11/1989 | Martini et al. | 264/514 |
| 4,882,412 | 11/1989 | Weaver et al. | 528/190 |
| 4,892,922 | 1/1990 | Weaver et al. | 528/190 |
| 4,892,923 | 1/1990 | Weaver et al. | 528/190 |
| 4,966,959 | 10/1990 | Cox et al. | 528/272 |

FOREIGN PATENT DOCUMENTS

| | | |
|---|---|---|
| 0 387 167 | 9/1990 | European Pat. Off. . |
| 0 394 803 | 10/1990 | European Pat. Off. . |
| 1 045 649 | 11/1953 | France . |
| 1 515 727 | 6/1978 | United Kingdom . |

OTHER PUBLICATIONS

G. R. Brannock et al., *Macromolecules*, 23, pp. 5240–5250 (1990).

D. S. Hubbell et al., *J. Appl. Polym. Sci.*, 21, pp. 3035–3061 (1977).

R. D. Fields et al., "Proceedings of the Third Int. Biodegradation Symposium", Sharpley et al., Eds., *Applied Science*, Barking, England, pp. 775–784 (1976).

Reed and Gilding, *Polymer*, 22, p. 499 (1981).

Tokiwa and Suzuki, *J. Appl. Polymer Sci.*, 26, pp. 441–448 (1981).

Droscher and Horlbeck, *Ange. Makromol. Chemic*, 128, pp. 203–213 (1984).

A. M. Reed et al., *Trans. Am. Soc. Artif. Intern. Organs*, vol. XXIII, pp. 109–115 (1977).

F. Stutzenberger et al., *J. Appl. Bacteriology*, 61, pp. 225–233 (1986).

M. Kunioka et al., *Appl. Microbiol. Biotechnol.*, 30, pp. 569–573 (1989).

K. Fritzsche et al., *Makromol. Chem.*, 191, pp. 1957–1965 (1990).

M. J. de Smet, *Journal of Bacteriology*, pp. 870–878, May, 1983.

R. A. Gross et al., *Macromolecules*, 22, pp. 1106–1115 (1989).

H. Brandl et al., *Int. J. Biol. Macromol.*, 11, pp. 49–55 (1989).

L. G. Ljungdahl et al., *Current Microbiology*, 9, pp. 195–200 (1983).

*Primary Examiner*—Peter A. Szekely
*Attorney, Agent, or Firm*—Betty J. Boshears; Harry J. Gwinnell

[57] ABSTRACT

This invention relates to binary blends of cellulose esters and aliphatic-aromatic copolyesters, cellulose esters and aliphatic polyesters as well as ternary blends of cellulose esters and/or aliphatic polyesters and/or aliphatic-aromatic copolyesters and/or polymeric compounds as well as fibers, molded objects, and films prepared therefrom.

1 Claim, 5 Drawing Sheets

ALIPHATIC-AROMATIC COPOLYESTERS AND CELLULOSE ESTER/POLYMER BLENDS

This is a continuation application of application Ser. No. 08/427,944 filed on Apr. 26, 1995, now U.S. Pat. No. 5,599,888 of Charles M. Buchanan, Robert M. Gardner, Matthew D. Wood, Alan W. White, Steven C. Gedon and Fred D. Barlow, Jr. for "ALIPHATIC-AROMATIC COPOLYESTERS AND CELLULOSE ESTER/POLYMER BLENDS", which is a divisional of Ser. No. 08/163,441 filed on Dec. 7, 1993 now U.S. Pat. No. 5,466,279 which is a divisional of Ser. No. 07/797,512 filed on Nov. 21, 1991, now U.S. Pat. No. 5,292,783 which issued on Mar. 8, 1994; which is a continuation-in-part of Ser. No. 07/736,262 filed on Jul. 23, 1991, now abandoned; which is a continuation-in-part of Ser. No. 07/620,225 filed on Nov. 30, 1990, now abandoned.

FIELD OF THE INVENTION

This invention concerns binary blends of cellulose esters with aliphatic polyesters or aliphatic-aromatic copolyesters as well as ternary blends of cellulose esters with aliphatic polyesters and/or aliphatic-aromatic copolyesters and/or other polymers. These resins are useful as molded or extruded plastic objects, fibers, or films. This invention also concerns random aliphatic-aromatic copolyesters which are useful as molded or extruded plastic objects, fibers, or films. Moreover, various additives can be added to the blends or to the random aliphatic-aromatic copolyesters to enhance properties such as water vapor transmission rates or biodegradability.

BACKGROUND OF THE INVENTION

It is well known that cellulose esters are important as commercial plastics and as fibers. In general, cellulose esters are used in plastic applications where hard but clear plastics are required. For example, cellulose esters are used in tool handles, eyeglass frames, toys, toothbrush handles, and the like. All of these applications require a combination of high melting and glass transition temperatures as well as high modulus and good tensile strength. Formulations based on cellulose esters which provide plastic films with low modulus but good tensile strength while maintaining sufficient melting and glass transition temperatures (Tg) to allow thermal processing are generally unknown. Formulations based on cellulose esters which allow thermal extrusion of fibers are also generally unknown.

Because of the high melt temperatures and low melt stability of many of the cellulose esters, plasticizers such as dioctyl adipate or triphenylphosphate are often added to the cellulose ester to lower the melt temperatures during melt processing of the polymer. Although this technique is effective, addition of a monomeric plasticizer often creates secondary problems related to volatile or extractable plasticizers such as dye drip during melt extrusion or long-term dimensional stability (creep) in an object made from the cellulose ester.

The most basic requirement for polymer-polymer miscibility is that the free energy of mixing be negative ($\Delta G<0$). Although on the surface it would seem that polymer-polymer miscibility would be common, in reality there are only a few known miscible binary blends and even fewer known miscible ternary blend systems (Brannock, G. R.; Paul, D. R., Macromolecules, 23, 5240–5250 (1990)). The discovery of miscible binary or ternary blends is very uncommon.

The classical experimental techniques for determining polymer blend miscibility involve the determination of the optical clarity of a film made from the blend, measurement of the appropriate mechanical properties, and measurement of the glass transition temperature by an appropriate thermal analysis technique such as dynamic mechanical thermal analysis (DMTA) or differential scanning calorimetry (DSC). If a blend is miscible, films made from the blend will generally be clear. Likewise, mechanical properties of a blend, such as tensile strength or tangent modulus, are often intermediate between those of the blend components. Furthermore, a miscible amorphous blend will show a single Tg intermediate between that of the component homopolymers while an immiscible or partially miscible blend will show multiple Tg's. In the case of a completely immiscible blend, the Tg's will be those of the homopolymers. For partially miscible blends, the Tg's will be intermediate values corresponding to partially miscible phases rich in one of the components. The variation in binary blend Tg can be modeled by the Fox-Flory equation, $Tg_{12}=Tg_1(W_1)+Tg_2(W_2)$, where $Tg_{12}$ is the Tg of the blend, $Tg_1$ and $Tg_2$ are the Tg's of homopolymers, and $W_1$ and $W_2$ are the weight percent of each component in the blend. Since the Fox equation does not take into account specific interaction between the blend components the Gordon-Taylor equation, $Tg_2=Tg_1+[kW_2(Tg_2-Tg_{12})/W_1]$ where k is a constant, is often preferred in blend analysis. For a homogenous, well mixed system, a plot of $Tg_{12}$ versus $W_2(Tg_2-Tg_{12})/W_1$ will yield a straight line the slope of which is equal to k and the ordinate intercept will be equal to $Tg_1$. The constant k is often taken as a measure of secondary interactions between the blend components. When k is equal to one, the Gordon-Taylor equation reduces to a simple weight average of the component Tg's.

Miscible blends of cellulose esters and other polymers are generally unknown. The most notable exceptions include the work disclosed by Koleske, et al. (U.S. Pat. No. 3,781,381 (1973)), Bogan and Combs (U.S. Pat. No. 3,668,157 (1972)), Waniczek et al., (U.S. Pat. No. 4,506,045 (1985)), and Wingler et al. (U.S. Pat. No. 4,533,397 (1985)). Koleske et al. reported that blends, formed by solution casting of polycaprolactone and cellulose ester mixtures, are miscible. Later work by Hubbell and Cooper (J. Appl. Polym. Sci., 1977, 21, 3035) demonstrated that cellulose acetate butyrate/polycaprolactone blends are in fact immiscible. Bogan and Combs have reported that block copolymers of polyether-polyesters form miscible blends with some cellulose esters. Critical to the invention of Bogan and Combs was the use of an elastomeric block copolymer; they report that the corresponding homopolymeric elastomers were incompatible with cellulose esters. Waniczek et al., have disclosed that polyester carbonates and polyether carbonates copolymers form miscible blends with many cellulose esters and are useful as thermoplastic resins. Wingler et al. report that contact lenses can be prepared from blends consisting of (A) 97–70% by weight of one or more cellulose esters and (B) 3–30% by weight of an aliphatic polymeric compound having ester moieties, carbonate moieties, or both ester and carbonate moieties in the same polymer chain. The invention of Wingler et al. is limited to aliphatic polymeric compounds; no reference is made to random copolymers consisting of aliphatic diacids, aromatic diacids, and suitable diols or polyols. The invention of Wingler is further limited to cellulose mixed esters having a weight per cent hydroxyl of 1.2% to 1.95% ($DS_{OH}=0.11-0.19$ where "DS" or "DS/AGU" refers to the number of substituents per anhydroglucose unit where the maximum DS/AGU is three). The invention of Wingler et al. is also limited to binary miscible blends and by the composition range of the blends (3–30% aliphatic polymeric compound). No reference is made to blends containing an immiscible component where the immiscible component is useful for enhancing properties such as water vapor transmission rates or biodegradability. Immiscible blends of cellulose esters and aromatic polyesters have also been disclosed by Pollock et al. (U.S. Pat. No. 4,770,931 (1988)) which are useful in applications such as paper substitutes.

One time use, disposable items are common. Examples of such disposable articles include items such as infant diapers, incontinence briefs, sanitary napkins, tampons, bed liners, bedpans, bandages, food bags, agricultural compost sheets, and the like. Examples of other disposable items include razor blade handles, toothbrush handles, disposable syringes, fishing lines, fishing nets, packaging, cups, clamshells, and the like. For disposable items, environmental non-persistence is desirable.

Disposable articles are typified by disposable diapers. A disposable diaper typically has a thin, flexible polyethylene film cover, an absorbent filler as the middle layer, and a porous inner liner which is typically nonwoven polypropylene. The diaper construction also requires tabs or tape for fastening the diaper (typically polypropylene) as well as various elastomers and adhesives. Although the absorbent filler is usually biodegradable or easily dispersed in an aqueous environment, currently neither the outer or inner liner nor the other parts such as the tabs or adhesives will degrade from microbial action. Consequently, disposable absorbent materials such as diapers accumulate in landfills and place enormous pressure on waste systems. Other disposable articles such as plastic bags or plastic compost sheets suffer from similar problems.

Numerous studies have demonstrated that cellulose or cellulose derivatives with a low degree of substitution, i.e., less than one, are biodegradable. Cellulose is degraded in the environment by both anaerobic or aerobic microorganisms. Typical endproducts of this microbial degradation include cell biomass, methane(anaerobic only), carbon dioxide, water, and other fermentation products. The ultimate endproducts will depend upon the type of environment as well as the type of microbial population that is present. However, it has been reported that cellulose esters with a DS greater than about one are completely resistant to attack by microorganisms. For example, Stutzenberger and Kahler (*J. Appl. Bacteriology,* 66, 225 (1986)) have reported that cellulose acetate is extremely recalcitrant to attack by *Thermomonospora curvata.*

Polyhydroxyalkanoates (PHA), such as polyhydroxybutyrate (PHB), polycaprolactone (PCL), or copolymers of polyhydroxybutyrate and polyhydroxyvalerate (PHBV), have been known for at least twenty years. With the exception of polycaprolactone, they are generally prepared biologically and have been reported to be biodegradable (M. Kunioka et al., *Appl. Microbiol. Biotechnol.,* 30, 569 (1989)).

Polyesters prepared from aliphatic diacids or the corresponding carboxylic ester of lower alcohols and diols have also been reported to be biodegradable. For example, Fields and Rodriguez ("Proceedings of the Third International Biodegradation Symposium", J. M. Sharpley and A. M. Kaplan, Eds., Applied Science, Barking, England, 1976, p. 775) prepared polyesters from C2–C12 diacids coupled with C4–C12 diols and found that many were biodegradable.

Aliphatic polyesters have been used in very few applications mainly because of their low melting points and low glass transition temperatures (generally less than 65° C. and −30° C., respectively). At room temperature, the physical form of many of the aliphatic polyesters is as a thick, viscous liquid. Therefore, aliphatic polyesters are not expected to be generally useful.

On the other hand, aromatic polyesters, such as poly (ethylene terephthalate), poly(cyclohexanedimethanol terephthalate), and poly(ethylene terephthalate-co-isophthalate), have proven to be very useful materials. Aromatic polyesters, however, are generally very resistant to biodegradation (J. E. Potts in "Kirk-Othmer Encyclopedia of Chemical Technology", Suppl. Vol, Wiley-Interscience, New York, 1984, pp. 626–668). Block copolyesters containing both aliphatic and aromatic structures have been prepared and have been shown to be biodegradable. Examples of aliphatic-aromatic block copolyester-ethers include the work of Reed and Gilding (*Polymer,* 22, 499 (1981)) using poly(ethylene terephthalate)/poly(ethylene oxide) where these block copolymers were studied and found to be biodegradable in vitro. Tokiwa and Suzuki have investigated block copolyesters such as those derived from poly-(caprolactone) and poly(butylene terephthalate) and found them to be degraded by a lipase (*J. Appl. Polym. Sci.,* 26, 441–448 (1981)). Presumably, the biodegradation is dependent upon the aliphatic blocks of the copolyesters; the blocks consisting of aromatic polyester are still resistant to biodegradation. Random aliphatic-aromatic copolyesters have not been investigated in this regard.

While random copolyesters with low levels of aliphatic diacids are known (e.g., Droscher and Horlbeck, *Ange. Makromol. Chemie,* 128, 203–213(1984)), copolyesters with high levels (>30%) of aliphatic dicarboxylic components are generally unknown. Copolyesters with as much as 40% aliphatic dicarboxylic acid components have been disclosed in adhesive applications; however, these copolyesters adhesives contain at least two dialcohol components in order to achieve the desired adhesive properties (Cox, A., Meyer, M. F., U.S. Pat. No. 4,966,959 (1990)).

There are many references to the preparation of films from polymers such as polyhydroxybutyrate (PHB). Production of films from PHB generally involves solvent casting principally because PHB polymers tend to remain sticky or tacky for a substantial time after the temperature has dropped below the melting point of the PHB. To circumvent this problem, Martini et al. (U.S. Pat. Nos. 4,826,493 and 4,880,592) teach the practice of co-extruding PHB with a thermoplastic that is non-tacky. Such thermoplastics remain as a permanent layer on the PHB film or may be a sacrificial film which is removed following extrusion.

PHB has also been reported to be useful in the preparation of disposable articles. Potts (U.S. Pat. Nos. 4,372,311 and 4,503,098) has disclosed that water soluble polymers such as poly(ethylene oxide) may be coated with biodegradable water insoluble polymers such as PHB. In these inventions, the PHB layer, which is distinct from the water soluble layer, degrades exposing the water soluble layer which will then disperse in an aqueous environment.

There have been other reports of the preparation of a biodegradable barrier film for use in disposable articles. Comerford et al. (U.S. Pat. No. 3,952,347) have disclosed that finely divided biodegradable materials such as cellulose, starch, carbohydrates, and natural gums may be dispersed in a matrix of nonbiodegradable film forming materials which are resistant to solubility in water. Wielicki (U.S. Pat. No. 3,602,225) teaches the use of barrier films made of plasticized regenerated cellulose films. Comerford (U.S. Pat. No.

3,683,917) teaches the use of a cellulosic material coated with a water repellent material.

There exists in the market place the need for thermoplastics which are useful in molding, fiber, and film applications. For these applications, it is desirable that the thermoplastic blend be processable at a low melt temperature and have a high glass transition temperature. These thermoplastics should not contain volatile or extractable plasticizers. Moreover, there is a need in the marketplace for a biodegradable material for use in disposable articles such as diapers, razors, and the like. As an example, unlike films prepared from polymers such as PHB, the material should be amenable to both solvent casting and melt extrusion. In melt extruding this material, coextrusion with other thermoplastics should not be a requirement. The barrier properties of this new biodegradable material should be adequate so that coating with a water insoluble polymer is not required. The new material should disperse completely in the environment and not require coating with a water soluble polymer. The mechanical properties of the material should be such that films of low modulus but of high tensile strength can be prepared.

SUMMARY OF THE INVENTION

The present invention, in part, concerns binary blends of cellulose esters and aliphatic-aromatic copolyesters, cellulose esters and aliphatic polyesters as well as ternary blends of cellulose esters and/or aliphatic polyesters and/or aliphatic-aromatic copolyesters and/or polymeric compounds as well as fibers, molded objects, and films prepared therefrom which have one or more of the above or below described desirable properties. More specifically, the present invention is directed to a blend comprising:

I. (A) about 5% to about 98% of a C1–C10 ester of cellulose having a DS/AGU of about 1.7 to 3.0 and an inherent viscosity of about 0.2 to about 3.0 deciliters/gram as measured at a temperature of 25° C. for a 0.5 g sample in 100 ml of a 60/40 parts by weight solution of phenol/tetrachloroethane, and (B) about 2% to about 95% of a aliphatic-aromatic copolyester having an inherent viscosity of about 0.2 to about 2.0 deciliters/gram as measured at a temperature of 25° C. for a 0.5 g sample in 100 ml of a 60/40 parts by weight solution of phenol/tetrachloroethane, said percentages being based on the weight of component (A) plus component (B);

II. (A) about 5% to about 98% of a C1–C10 ester of cellulose having a DS/AGU of about 1.7 to 2.75 and an inherent viscosity of about 0.2 to about 3.0 deciliters/gram as measured at a temperature of 25° C. for a 0.5 g sample in 100 ml of a 60/40 parts by weight solution of phenol/tetrachloroethane, and (B) about 2% to about 95% of a aliphatic polyester having an inherent viscosity of about 0.2 to about 2.0 deciliters/gram as measured at a temperature of 25° C. for a 0.5 g sample in 100 ml of a 60/40 parts by weight solution of phenol/tetrachloroethane, said percentages being based on the weight of component (A) plus component (B);

III. (A) about 4% to about 97% of a C1–C10 ester of cellulose having a DS/AGU of about 1.7 to 3.0 and an inherent viscosity of about 0.2 to about 3.0 deciliters/gram as measured at a temperature of 25° C. for a 0.5 g sample in 100 ml of a 60/40 parts by weight solution of phenol/tetrachloroethane, (B) about 2% to about 95% of an aliphatic polyester and/or an aliphatic-aromatic copolyester having an inherent viscosity of about 0.2 to about 2.0 deciliters/gram as measured at a temperature of 25° C. for a 0.5 g sample in 100 ml of a 60/40 parts by weight solution of phenol/tetrachloroethane, (C) about 1% to about 94% of immiscible, partially miscible, or miscible polymeric compounds having an inherent viscosity of about 0.2 to about .2.0 deciliters/gram as measured at a temperature of 25° C. for a 0.5 g sample in 100 ml of a 60/40 parts by weight solution of phenol/tetrachloroethane, said percentages being based on the weight of component (A) plus component (B) plus component (C);

IV. (A) about 50% to about 99% of a binary blend of (I) or (II) or a ternary blend of (III) having an inherent viscosity of about 0.4 to about 3.0 deciliters/gram as measured at a temperature of 25° C. for a 0.5 g sample in 100 ml of a 60/40 parts by weight solution of phenol/tetrachloroethane, (B) about 1% to about 50% of biodegradable additives, said percentages being based on the weight of component (A) plus component (B);

V. (A) about 95% to about 99.95% of a binary blend of (I) or (II) or a ternary blend of (III) having an inherent viscosity of about 0.4 to about 3.0 deciliters/gram as measured at a temperature of 25° C. for a 0.5 g sample in 100 ml of a 60/40 parts by weight solution of phenol/tetrachloroethane, (B) about 0.05% to about 5% of immiscible hydrophobic agent, said percentages being based on the weight of component (A) plus component (B).

The present invention is also directed to:

VI. An essentially linear, random, semicrystalline aliphatic-aromatic copolyester which has an inherent viscosity of about 0.5 to 1.8 deciliters/gram as measured at a temperature of 25° C. for a 0.5 g sample in 100 mL of a 60/40 parts by weight solution of phenol/tetrachloroethane and has a melting point between 75° C. and 160° C.

VII. A mixture of 50 to 99% of (VI) and about 1% to about 50% of biodegradable additives, said percentages being based on the weight of component (VI) plus biodegradable additives.

DETAILED DESCRIPTION OF THE INVENTION

Figure 1A:
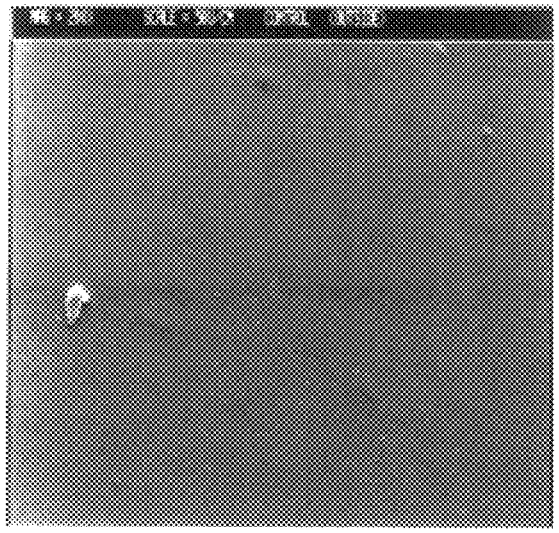
FIG. 1A—Scanning electron microscopy (SEM) photograph of the outer, smooth surface of a cellulose acetate (DS=1.7) film formed by drawing a film from a 20 wt. % solution of cellulose acetate in a 50/50 (vol./vol.) mixture of water acetone. Magnification is 200×.

We have found that cellulose esters form binary blends with aliphatic polyesters and aliphatic-aromatic copolyesters as well as ternary blends with aliphatic polyesters/polyacrylates, aliphatic polyesters/polyvinyl acetates, aliphatic polyesters/polyvinyl alcohol, aliphatic polyesters/polyvinyl chloride, aliphatic polyesters/polycarbonates, aliphatic polyesters/polyvinyl acetate-polyethylene copolymer, aliphatic polyesters/cellulose ethers, aliphatic polyesters/polyamides, aliphatic-aromatic copolyesters/polyacrylates, aliphatic-aromatic copolyesters/polyvinyl acetates, aliphatic-aromatic copolyesters/polyvinyl alcohol, aliphatic-aromatic copolyesters/polyvinyl chloride, aliphatic-aromatic copolyesters/polycarbonates, aliphatic-aromatic copolyesters/polyvinyl acetate-polyethylene copolymer, aliphatic-aromatic copolyesters/cellulose ethers, or aliphatic-aromatic copolyesters/polyamides, as well as other polymers, to produce resins which are useful as molded or extruded plastic objects, fibers, or films. Moreover, various additives can be added to the blend to enhance properties such as water vapor transmission rates or biodegradability.

The cellulose esters of the present invention generally comprise repeating units of the structure:

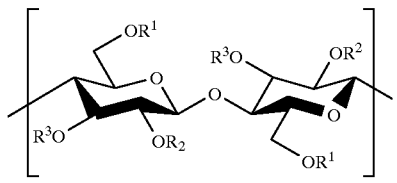

wherein $R^1$, $R^2$, and $R^3$ are selected independently from the group consisting of hydrogen or straight chain alkanoyl having from 2 to 10 carbon atoms.

The cellulose esters useful in formulating the blend can be a cellulose triester or a secondary cellulose ester. Examples of cellulose triesters include cellulose triacetate, cellulose tripropionate, or cellulose tributyrate. Examples of secondary cellulose esters include cellulose acetate, cellulose acetate propionate, and cellulose acetate butyrate. These cellulose esters are described in U.S. Pat. Nos. 1,698,049; 1,683,347; 1,880,808; 1,880,560; 1,984,147, 2,129,052; and 3,617,201, incorporated herein by reference in their entirety.

The cellulose esters useful in the present invention can be prepared using techniques known in the art or are commercially available, e.g., from Eastman Chemical Company, Inc., Kingsport, Tenn., U.S.A.

The cellulose esters useful in the present invention have at least 2 anhydroglucose rings and typically have between 2 and 5,000 anhydroglucose rings; also, such polymers typically have an inherent viscosity (IV) of about 0.2 to about 3.0 deciliters/gram, preferably about 1 to about 1.5, as measured at a temperature of 25° C. for a 0.5 gram sample in 100 ml of a 60/40 by weight solution of phenol/tetrachloroethane. In addition, the DS/AGU of the cellulose esters useful herein ranges from about 1.7 to about 3.0. Preferred esters of cellulose include cellulose acetate (CA), cellulose propionate (CP), cellulose butyrate (CB), cellulose acetate propionate (CAP), cellulose acetate butyrate (CAB), cellulose propionate butyrate (CPB), and the like. CAP and CAB are more preferred cellulose esters. The most preferred ester of cellulose is CAP.

For binary blends, the preferred esters of cellulose for blending with aliphatic-aromatic copolyesters are CAP and CAB. The preferred ester of cellulose is CAP having a DS/AGU of 2.1–2.85 wherein the DS/AGU of acetyl ester is 1–50% of the total ester content. The most preferred CAP's have a DS/AGU of 2.5–2.75 wherein the DS/AGU of acetyl ester is 4–30% of the total ester content.

For binary blends, the preferred esters of cellulose for blending with aliphatic polyesters are CA, CAP, and CAB. A preferred ester of cellulose is CA having a DS/AGU of 1.7–2.75. Another preferred ester of cellulose is CAP having a DS/AGU of 1.7–2.75 wherein the DS/AGU of acetyl ester is 1–50% of the total ester content. The most preferred CAP's have a DS/AGU of 2.1–2.6 wherein the DS/AGU of acetyl ester is 4–30% of the total ester content. It is also preferred that the CAP's have a glass transition temperature (Tg) of about 140° C. to 180° C.

For ternary blends, the preferred esters of cellulose for blending with aliphatic polyesters and/or aliphatic-aromatic copolyesters and/or polymeric compounds, biodegradable additives, or hydrophobic agents are CAP and CAB. The preferred ester of cellulose is CAP having a DS/AGU of 1.7–3.0 wherein the DS/AGU of acetyl ester is 1–50% of the total ester content. The most preferred CAP's have a DS/AGU of 2.5–2.75 wherein the DS/AGU of acetyl ester is 4–30% of the total ester content.

The aliphatic-aromatic copolyesters that are useful in blends in the present invention are random copolymers and preferably comprises repeating units of:

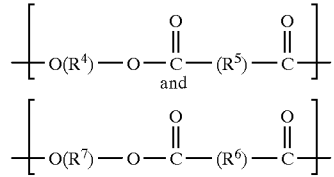

wherein $R^4$ and $R^7$ are selected from one or more of the following groups consisting of $C_2$–$C_{12}$ alkylene or oxyalkylene; $C_2$–$C_{12}$ alkylene or oxyalkylene substituted with one to four substituents independently selected from the group consisting of halo, $C_6$–$C_{10}$ aryl, and $C_1$–$C_4$ alkoxy; $C_5$–$C_{10}$ cycloalkylene; $C_5$–$C_{10}$ cycloalkylene substituted with one to four substituents independently selected from the group consisting of halo, $C_6$–$C_{10}$ aryl, and $C_1$–$C_4$ alkoxy; $R^5$ is selected from one or more of the following groups consisting of $C_0$–$C_{12}$ alkylene or oxyalkylene; $C_1$–$C_{12}$ alkylene or oxyalkylene substituted with one to four substituents independently selected from the group consisting of halo, $C_6$–$C_{10}$ aryl, and $C_1$–$C_4$ alkoxy; $C_5$–$C_{10}$ cycloalkylene; and $C_5$–$C_{10}$ cycloalkylene substituted with one to four substituents independently selected from the group consisting of halo, $C_6$–$C_{10}$ aryl, and $C_1$–$C_4$ alkoxy; $R^6$ is selected from one or more of the following groups consisting of $C_6$–$C_{10}$ aryl, $C_6$–$C_{10}$ aryl substituted with substituted with one to four substituents independently selected from the group consisting of halo, $C_1$–$C_4$ alkyl, and $C_1$–$C_4$ alkoxy.

It is preferred that said aliphatic-aromatic copolyester comprises 10 to 1,000 repeating units. Most preferred is when said aliphatic-aromatic copolyester comprises 15 to 600 repeating units.

In the present invention, the mole % of $R^5$ in the copolymer can range from 30 to 95%, and the mole % of $R^6$ can range from 5 to 70%. A more preferred range is when the mole % of $R^5$ is from about 45 to 85% and the mole % of $R^6$ is from about 15–55 mol %. The most preferred ranges, in general, depend upon the needed level of miscibility of the copolyester with the cellulose esters and the physical properties desired. The most preferred ranges for miscible blends is when $R^5$ is glutaric and the mole % of $R^5$ in the copolyester ranges from 70 to 85% and the mole % of $R^6$ range from 15–30 mol %. The most preferred ranges for partially miscible blends is when $R^5$ is glutaric and the mol % of $R^5$ in the copolyester ranges from 45 to 60% and the mole % of $R^6$ ranges from 40–55 mol %. The range of miscibility of a particular blend can change as the molecular weight of a blend component is changed. In general, an aliphatic-aromatic polyester having a lower molecular weight or inherent viscosity will be more miscible with a given cellulose ester relative to the higher molecular weight polyester.

It is preferred that the aliphatic-aromatic copolyester has an inherent viscosity of about 0.4 to about 1.2 as measured at a temperature of 25° C. for a 0.5 gram sample in 100 ml of a 60/40 by weight solution of phenol/tetrachloroethane.

As used herein the terms "alkyl" and "alkylene" refer to either straight or branched chain moieties such as —$CH_2$—$CH_2$—$CH_2$—$CH_2$— and —$CH_2CH(X)$—$CH_2$—. Also, all of the carbon atoms of the cycloalkyl and cycloalkylene moieties are not necessarily in the ring structure, e.g., a $C_8$ cycloalkyl group can be cyclooctyl or dimethylcyclohexyl. The term "oxyalkylene" refers to alkylene chains containing from 1 to 4 ether oxygen groups.

One type of aliphatic polyesters useful in the present invention preferably comprises repeating units of:

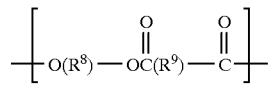

wherein $R^8$ is selected from one or more of the following groups consisting of $C_2$–$C_{12}$ alkylene or $C_2$–$C_{12}$ oxyalkylene; $C_2$–$C_{12}$ alkylene or $C_2$–$C_{12}$ oxyalkylene substituted with one to four substituents independently selected from the group consisting of halo, $C_6$–$C_{10}$ aryl, and $C_1$–$C_4$ alkoxy; $C_5$–$C_{10}$ cycloalkylene; $C_5$–$C_{10}$ cycloalkylene substituted with one to four substituents independently selected from the group consisting of halo, $C_6$–$C_{10}$ aryl, and $C_1$–$C_4$ alkoxy; $R^9$ is selected from one or more of the following groups consisting of $C_0$–$C_{12}$ alkylene or oxyalkylene; $C_1$–$C_{12}$ alkylene or oxyalkylene substituted with one to four substituents independently selected from the group consisting of halo, $C_6$–$C_{10}$ aryl, and $C_1$–$C_4$ alkoxy; $C_5$–$C_{10}$ cycloalkylene; and $C_5$–$C_{10}$ cycloalkylene substituted with one to four substituents independently selected from the group consisting of halo, $C_6$–$C_{10}$ aryl, and $C_{1C4}$ alkoxy.

It is preferred that $R^8$ is $C_2$–$C_6$ alkylene, $C_4$–$C_8$ oxyalkylene, or $C_5$–$C_{10}$ cycloalkylene; and $R^9$ is $C_0$–$C_{10}$ alkylene, $C_2$ oxyalkylene or $C_5$–$C_{10}$ cycloalkylene.

It is more preferred that $R^8$ is $C_2$–$C_4$ alkylene, $C_4$–$C_8$ oxyalkylene, or $C_5$–$C_{10}$ cycloalkylene; and $R^9$ is $C_2$–$C_4$ alkylene, $C_2$ oxyalkylene or $C_5$–$C_{10}$ cycloalkylene.

It is preferred that said aliphatic polyester comprises 10 to 1,000 repeating units. Most preferred is when said aliphatic polyester comprises 15 to 600 repeating units. The terms "alkyl" and "alkylene" are as defined above.

A second type of aliphatic polyester are polyhyroxyalkanoates which are comprised of repeat units of the following structure:

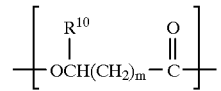

wherein m is an integer of 0 to 10, and $R^{10}$ is selected from the group consisting of hydrogen; $C_1$–$C_{12}$ alkyl; $C_1$–$C_{12}$ alkyl substituted with one to four substituents independently selected from the group consisting of halo, $C_6$–$C_{10}$ aryl, and $C_1$–$C_4$ alkoxy; $C_5$–$C_{10}$ cycloalkyl; and $C_5$–$C_{10}$ cycloalkyl substituted with one to four substituents independently selected from the group consisting of halo, $C_6$–$C_{10}$ aryl, and $C_1$–$C_4$ alkoxy.

For the purpose of this invention aliphatic polyester is defined as an aliphatic polyester which does not contain significant quantities of carbonate linkages. Furthermore, polyester is defined as a polyester prepared by a condensation process or by a biological process.

Typical polymeric compounds for ternary blends include polyacrylates such as polymethyl methacrylate (PMMA), polyethyl methacrylate (PEMA), or copolymers thereof such as those which are commercially available from Rohm and Haas. Polyvinyl acetate, polyvinyl alcohol, polyvinyl chloride, and polyvinyl acetate-polyethylene copolymers are also useful in ternary blends and are common commercial polymers which are available from companies such as Air Products and Chemicals, Inc. Polycarbonates, available from GE Plastics, are also useful in ternary blends. Cellulose ethers are commercially available from companies such as Aqualon Co. and are also useful in ternary blends. Polyamides, e.g., nylon 6 which is available from Ashley Polymers, Inc., is also highly useful in ternary blends. For this invention, preferred polyacrylates are PMMA. The preferred polyvinyl alcohols are those that are 5–60% hydrolyzed and have a molecular weight of 1,000 to 30,000. The preferred cellulose esters are hydroxypropyl cellulose (HPC) and hydroxypropyl methyl cellulose (HPMC). The preferred polyvinyl acetate will have a molecular weight of 1,000 to 1,000,000.

Typical biodegradable additives for binary and ternary blends of this invention include microcrystalline cellulose, cellulose monoacetate, starch and other carbohydrates. The preferred materials are microcrystalline cellulose, available from FMC, or starch, available from National Starch Co., which typically have a particle size of 1–200 microns; the preferred particle size is 0.1–15 microns. Also preferred are cellulose monoacetates which have a DS/AGU of 1.2 to 0.4 and will be either water soluble or water swellable (U.S. Pat. No. 509,385; 509,400 (1990)).

Typical immiscible hydrophobic agents include paraffin, monoacyl carbohydrates, and monoglycerides. An example of a monoacyl carbohydrate is 6-O-steryl-glucopyranoside. The preferred hydrophobic agents are monoglycerides containing C12–C18 fatty acids. These monoglycerides containing C12–C18 fatty acids may also be optionally acylated with 5–95% acetyl, propionyl, butyryl, or succinyl groups. The more preferred monoglycerides are those containing C16–C18 fatty acids. The most preferred hydrophobic agent is glyceryl monostearate.

The preparation of polyesters and copolyesters is well known in the art (U.S. Pat. No. 2,012,267, incorporated herein by reference in its entirety). Such reactions are usually carried out at temperatures from 150° C. to 300° C. in the presence of polycondensation catalysts such as titanium tetrachloride, manganese diacetate, antimony oxide, dibutyl tin diacetate, zinc chloride, or combinations thereof. The catalysts are typically employed in amounts between 10 to 1000 ppm, based on total weight of the reactants. For the purpose of the present invention, a representative aliphatic polyester is the polycondensation product of dimethylglutarate and 1,6-hexanediol. This polyester, poly(hexamethylene glutarate), is produced when dimethylglutarate and 1,6-hexanediol are heated at approximately 210° C. for 4 hours and then at 260° C. for 1.5 hours under vacuum in the presence of 100 ppm of Ti. A representative aliphatic-aromatic copolyester is poly(tetramethylene glutarate-co-terephthalate) containing 30 mole per cent terephthalate. This polyester is produced when dimethylglutarate, dimethyl terephthalate, and 1,4-butanediol are heated at 200° C. for 1 hour then at 245° C. for 0.9 hour under vacuum in the presence of 100 ppm of Ti present initially as $Ti(O^iPr)_4$.

It is preferred that said aliphatic-aromatic copolyester for use in blending is prepared from any polyester forming combination of dicarboxylic acids or derivatives thereof, and diols. Said dicarboxylic acids are selected from the group consisting of the following diacids: malonic, succinic, glutaric, adipic, pimelic, azelaic, sebacic, fumaric, 2,2-dimethyl glutaric, suberic, 1,3-cyclopentanedicarboxylic, 1,4-cyclohexane-dicarboxylic, 1,3-cyclohexanedicarboxylic, diglycolic, itaconic, maleic, 2,5-norbornanedicarboxylic, 1,4-terephthalic, 1,3-terephthalic, 2,6-naphthoic, 1,5-naphthoic, and ester forming derivatives thereof, and combinations thereof; and said diols are selected from the group consisting of ethylene glycol, diethylene glycol, propylene glycol, 1,3-propanediol, 2,2-dimethyl-1,3-propanediol, 1,3-butanediol, 1,4-butanediol, 1,5-pentanediol, 1,6-hexanediol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, triethylene glycol, tetraethylene glycol, and combinations thereof.

Specific examples of preferred aliphatic-aromatic copolyesters for blending include poly(tetramethylene glutarate-co-terephthalate-co-diglycolate) [50/45/5], poly(tetramethylene glutarate-co-terephthalate) [50/50], poly(tetramethylene glutarate-co-terephthalate) [60/40], poly(tetramethylene glutarate-co-terephthalate) [70/30], poly(tetramethylene glutarate-co-terephthalate) [85/15], poly(ethylene glutarate-co-terephthalate) [70/30], poly(tetramethylene adipate-co-terephthalate) [85/15], poly(tetramethylene succinate-co-terephthalate) [85/15], and poly(tetramethylene-co-ethylene glutarate-co-terephthalate) [50/50,70/30].

The aliphatic-aromatic copolyesters (referred to as AAPE herein) that are useful in the present invention without requiring blending of a significant amount of another component are essentially linear, random copolymers and preferably comprise repeating units of:

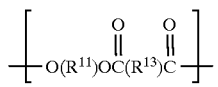

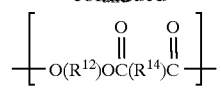

wherein $R^{11}$ and $R^{12}$ are the same and are selected from the groups consisting of C2–C8 alkylene or oxylalkylene; $R^{13}$ is selected from one or more of the groups consisting of C0–C8 alkylene or C2–C4 oxyalkylene, and the mole % of $R^{13}$ is from about 95–35%; $R^{14}$ is selected from the group of C6–C10 aryl, and the mole % of $R^{14}$ is from about 5–65%. More preferred AAPE are those wherein $R^{11}$ and $R^{12}$ are the same and are selected from C2–C4 alklyene; $R^{13}$ is selected from one or more of the groups consisting of C2–C6 alkylene or C2 oxyalkylene, and the mole % of $R^{13}$ is from about 95–40%; $R^{14}$ is 1,4-disubstituted-C6 aryl, and the mole % of $R^{14}$ is from about 5–60%. The most preferred compositions for these AAPE are those prepared from the following diols and diacids (or polyester forming derivatives thereof) in the following mole %:

(1) Glutaric acid (30–65%); diglycolic acid (0–10 mol %); terephthalic acid (25–60%); 1,4-butanediol (100 mole %).

(2) Succinic acid (30–85%); diglycolic acid (0–10%); terephthalic acid (5–60%); 1,4-butanediol (100 mole %).

(3) Adipic acid (30–65%); diglycolic acid (0–10%); terephthalic acid (25–60%); 1,4-butanediol (100 mole %).

Specific examples of preferred AAPE for applications where blending is not required include poly(tetramethylene glutarate-co-terephthalate-co-diglycolate) [50/45/5], poly(tetramethylene glutarate-co-terephthalate) [50/50], poly(tetramethylene glutarate-co-terephthalate) [60/40], poly(tetra-methylene glutarate-co-terephthalate) [40/60], poly(tetramethylene succinate-co-terephthalate) [85/15], poly(ethylene succinate-co-terephthalate) [70/30], poly(tetramethylene adipate-co-terephthalate) [85/15], and poly(tetramethylene succinate-co-terephthalate) [70/30].

It is preferred that said aliphatic polyester is prepared from any polyester forming combination of the following:

(i) hydroxy acids, (ii) dicarboxylic acids or derivatives thereof, and (iii) diols.

Said hydroxy acids are selected from the group consisting of 4-(hydroxymethyl)cyclohexanecarboxylic acid, hydroxypivalic acid, 6-hydroxyhexanoic acid, glycolic acid, lactic acid, ester forming derivatives thereof, and combinations thereof; said dicarboxylic acids are selected from the group consisting of the following diacids: malonic, succinic, glutaric, adipic, pimelic, azelaic, sebacic, fumaric, 2,2-dimethyl glutaric, suberic, 1,3-cyclo-pentanedicarboxylic, 1,4-cyclohexanedicarboxylic, 1,3-cyclohexane-dicarboxylic, diglycolic, itaconic, maleic, 2,5-norbornanedicarboxylic, ester forming derivatives thereof, and combinations thereof; and said diols are selected from the group consisting of ethylene glycol, propylene glycol, 1,3-propanediol, 2,2-dimethyl-1,3-propanediol, 1,3-butanediol, 1,4-butanediol, 1,5-pentanediol, 1,6-hexanediol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, diethylene glycol, triethylene glycol, tetraethylene glycol, and combinations thereof.

Specific examples of preferred aliphatic polyesters include, polyhydroxybutyrate, a copolymer of polyhydroxybutyrate and polyhydroxyvalerate, poly(hexamethylene glutarate), poly(hexamethylene adipate), poly(ethylene sebacate), poly(tetramethylene glutarate), poly(tetramethylene adipate), poly(tetramethylene sebacate), poly(ethylene glutarate), poly(ethylene succinate), poly(tetramethylene succinate), or poly(ethylene adipate).

Other aliphatic polyesters useful in the present invention are polyhydroxyalkanoates that are derived from biological sources. A number of laboratories (cf. *Makromol. Chem.*, 191, 1957–1965 (1990); *J. Bacteriol.*, 154, 870 (1983); *Macromolecules*, 22, 1106 (1989)) have demonstrated that microorganisms, e.g., *Pseudomonas oleovorans, Alcaligenes eutrophus, Bacillus megaterium, Rhodospirillum rubrum*, can accumulate polyhydroxy-alkanoates containing alkyl pendant groups when grown on either n-alkanes or n-alkanoic acids under nutrient limiting conditions. In the case of *P. oleovorans*, a polyhydroxyalkanoate with a phenyl pendant group can be produced. The polymer forms as intracellular granules which provides the cell with a reserve of fatty acid in a form that is osmotically inert. When the microorganism is faced with energy or starvation conditions the polymer is degraded as a food source; hence, bacterial polyhydroxyalkanoates are inherently biodegradable.

Polyhydroxyalkanoates derived from biological sources are rarely homopolymers. During biosynthesis, carbon segments, typically two carbon fragments, are either removed or added to the original alkanoate resulting in the formation of a copolymer (*Int. J. Biol. Macromol.*, 11, 49–55 (1989)). For example, when *P. oleovorans* is fed either n-octane or n-octanoic acid as the only carbon source, the product produced is a copolymer which contains mostly C6 and C8 units.

Any of the blends, AAPEs, films, plastic objects, and fibers of the invention can optionally additionally comprise 0.001 to 50 weight per cent, based on the total weight of the composition, of at least one additional additive selected from a non-polymeric plasticizer, a thermal stabilizer, an antioxidant, a pro-oxidant, an acid scavenger, an ultraviolet light stabilizer, a promoter of photodegradation, inorganics, and colorants. Typical non-polymeric plasticizers include dioctyl adipate, phosphates, and diethyl phthalate. Representative inorganics include talc, $TiO_2$, $CaCO_3$, $NH_4Cl$, and silica. Colorants can be monomeric, oligomeric, and, of course, polymeric. Preferred polymeric colorants are aliphatic polyesters, aliphatic-aromatic copolyesters, or aromatic polyesters in which the color producing monomer, i.e., a dye, is covalently incorporated into the polymer. Such representative polymeric colorants are described by Weaver et al. in U.S. Pat. Nos. 4,892,922, 4,892,923, 4,882,412, 4,845,188, 4,826,903, and 4,749,773 and are incorporated herein by reference in their entirety. These polymeric dyes are represented by poly(tetramethylene terephthalate) containing 10% 1,5-bis(O-carboxyanilino) anthraquinone.

Of course, it is also preferred, but not required, that the blends of the invention, as well as the films, plastic objects, and fibers prepared from the blends, be compatible and/or biodegradable. The preferred blends, films, plastic objects, and fibers are compatible as evidenced by improved mechanical properties, having a single Tg, and/or being substantially clear or substantially non-hazy. It is also preferred, but not required, that the AAPE, as well as the films, plastic objects, and fibers prepared from the AAPE be biodegradable.

Films made from the blends have good tensile properties and can be very flexible depending upon the type of cellulose ester and aliphatic polyesters, aliphatic-aromatic copolyesters, and/or polymeric compound selected. Many of the films have good optical properties, i.e., are preferably substantially clear; the films can also contain significant quantities of colorant (i.e., pigment or dye). Because these films can contain dyes or pigments, extensive purification of PHA, such as PHB, to remove cellular material is not required.

For film used in environmentally non-persistent applications, it is preferred that the blend used to make the film be comprised of a cellulose ester with a DS of (2.1–2.75) and with a high Tg (140–180° C.). Since the blends of this invention generally exhibit a Tg which can be predicted from the equation, $Tg_{12}=Tg_1 W\%_1+Tg_2 W\%_2$, use of a cellulose ester with a higher Tg permits the incorporation of more polyester into the blend than is possible when using a cellulose ester with a lower Tg while still maintaining equivalent blend Tg's. Moreover, we have surprisingly found that because the lower DS cellulose ester generally has a higher modulus, incorporation of more polyester in the blend with the low DS cellulose ester leads to films with equivalent mechanical properties to films made from blends composed of a cellulose ester with a lower Tg and lower polyester content. Incorporation of more polyester in the blend is highly desirable since the blends with higher polyester content will biodegrade at a faster rate.

Of course, many of the AAPEs of this invention which do not require blending are also useful in film applications. While these AAPE do not have as high as a melting point as poly(ethylene terephthalate), the AAPE have higher melting points that are generally observed with aliphatic polyesters and are therefore useful in many applications, particularly those requiring biodegradability. Succinic acid based AAPEs show particularly good utility in these applications due to their relatively high melting points. These copolyesters have been shown to be degradable even though they are semicrystalline and contain substantial amounts of aromatic groups. Furthermore, diglycolic acid has been found to be a useful comonomer for these AAPE because it aids in the initial breakup of the films.

These AAPEs are also particularly useful in molded parts, extruded objects, fibers, non-wovens, and foamed objects which benefit from being biodegradable. Films and fibers made from these copolyesters can be oriented. Orientation in many of these copolymers (especially those containing 1,4-butanediol) is accompanied by improved physical properties and a change from being opaque to being clear. AAPE films can be oriented uniaxially or biaxially and can be oriented in a blown film operation.

The blends and/or AAPE of this invention are useful in packaging applications where thin films are desirable. Many of the blends and/or AAPE of this invention are particularly useful as thin barrier films where they must function as a barrier and/or be biodegradable. For example, these blends are useful as protective barrier films and may be used in disposable absorbent articles such as infant diapers, incontinence briefs, sanitary napkins, tampons, bed liners, bedpan liners, bandages, and the like. It is preferred that the films of the invention have a tangent modulus of $2.5 \times 10^5$ psi to $0.01 \times 10^5$ psi, a tensile strength of at least about $0.5 \times 10^3$ psi, an average tear force of at least about 7.0 g/mil, and an elongation at break of at least about 5%. Also preferred is wherein said films have a thickness of about 0.1 mil to about 20 mil and a water vapor transmission rate less than about 500 g mil/m²-24 hours.

The blends and/or AAPEs of this invention can also be used in the other parts of disposable diapers. In addition to being used as a protective barrier film, these blends and/or AAPEs can be used as tabs, nonwovens, fibers, tape, and other parts needed in the construction of a diaper.

We have found that films prepared from these binary and ternary blends of cellulose esters as well as from AAPEs have desirable moisture barrier properties. With the blends, the specific rates can be modified by modification of the blend composition. For example, the water vapor transmission rates can be controlled by the amount of aliphatic polyester, aliphatic-aromatic copolyester, or polymeric compounds present in the binary or ternary blends. The water vapor transmission rates can also be controlled by the amount of aromatic dicarboxylic acid monomer present in the aliphatic-aromatic copolyester component of the blend. Of course, the water vapor transmission rates of the blends can be additionally controlled by the addition of an immiscible hydrophobic agent.

The blends and/or AAPEs of this invention are also useful as molded plastic parts or as solid, foamed plastic objects. Examples of such parts include eyeglass frames, toothbrush handles, toys, automotive trim, tool handles, camera parts, razor parts, ink pen barrels, disposable syringes, bottles, and the like. The plastic parts, especially those made by a foamed method which gives the plastic part increased surface area, of this invention are particularly useful in applications were it is desired that the plastic part be environmentally non-persistent. Injection molding bars made from the blends and/or AAPE of the invention typically have a flexural modulus of $5.0 \times 10^5$ psi to $0.1 \times 10^5$ psi, a flexural strength of $13 \times 10^3$ psi to $0.1 \times 10^3$ psi, and a notched Izod (23° C.) of 1.0 to 25 ft-lb/in. It is preferred that the molding bars have a flexural modulus of $3.8 \times 10^5$ psi to $1.5 \times 10^5$ psi, a flexural strength of $11.4 \times 10^3$ psi to $4 \times 10^3$ psi, and a notched Izod (23° C.) of 2 to 15 ft-lb/in.

The blends and/or AAPE of this invention are also useful as fibers. Examples of fiber applications include cigarette filters, diaper topsheet, sanitary napkins, fishing line, fishing nets, fiber for producing surgical clothing, hygiene articles, absorbent fibers, fibers for conveying liquids, and the like. We have found that, in addition to being spun from an appropriate solvent, the blends and/or AAPE of this invention can be melt-spun to produce fibers with excellent strength. The fibers can be oriented by drawing the fiber after spinning or by orientation during the spinning (cabinet orientation). Fibers produced from the blends and/or AAPEs have excellent shape retention even for fibers with complex cross-sectional shapes. We have also found that the fibers can be readily crimped. Fiber produced from the blends and/or AAPEs typically have a denier/filament (DPF) of 30–0.1. The preferred denier is 10–1.5 DPF. For fluid management, the fiber can contain hydrophobic agents or, optionally, can be coated with hydrophobic agents.

The blends, films, plastic objects, and fibers prepared from the blends of the invention have a melt temperature between about 120° C. and about 280° C. The preferred melt temperature range from 150° C. to 190° C. Also, such blends, films, plastic objects, and fibers have a glass transition temperature (Tg) as measured by differential scanning calorimetry (DSC) or dynamic mechanical thermal analysis (DMTA) of about 25° C. to about 200° C. The preferred range for the glass transition temperatures is 50° C. to 100° C. The blends and films are also preferably non-tacky.

The preferred AAPE of this invention and products made therefrom have melting points between 75° C. and 160° C. The more preferred range is between 80° C. and 140° C.

For the blends of the invention containing cellulose esters and aliphatic-aromatic copolyesters, the preferred level of polyester in the blend depends, in general, upon the desired level of miscibility of the blend and upon the needed physical properties. A preferred range is when component I(B) is present in an amount of about 5% to about 75% and component I(A) is present in an amount of about 25% to about 95% and that component I(A) have a DS of 2.1–2.75. When it is desirable to have higher tensile strength, flexural strength, and flexural modulus in molded plastic objects and the like, a more preferred range is when component I(B) is present in an amount of about 5% to about 25% and that component I(B) has an I.V. of 0.2–2.0 and component I(A) is present in an amount of about 75% to about 95% and that component I(A) have a DS of 2.1–2.75. When it is desirable that the blend used for the molded plastic part be miscible, that is optically clear, it is preferred that component I(B) have an I.V. of 0.3–0.6 and be present in the amount of 5–25%.

When it is desirable to have lower modulus blends for applications such as films, bottles, fiber, and the like, a more preferred range is when component I(B) is present in an amount of about 30% to about 75% and component I(A) is present in an amount of about 25% to about 70% and that component I(A) have a DS of 2.1–2.75. When it is desirable to have a miscible blend useful in films, bottles, fiber, and the like, a more preferred range is when component I(B) is present in an amount of about 30% to about 55%, $R^5$ is glutaric present in the 70–85% range, and component I(A) is present in an amount of about 45% to about 70% and that component I(A) have a DS of 2.5–2.75. The most preferred partially miscible blend useful in films is when component I(B) is present in an amount of about 60% to about 75%, $R^5$ is glutaric present in the 45–60% range, and component I(A) is present in an amount of about 25% to about 40% and that component I(A) have a DS of 2.5–2.75.

For the blends of the invention containing cellulose esters and aliphatic polyesters it is preferred that component II(B) is present in an amount of about 10% to about 60% and component II(A) is present in an amount of about 40% to about 90% and that component II(A) have a DS of 2.1–2.7. Most preferred is when component II(B) is present in an amount of about 35% to about 55% and component II(A) is present in an amount of about 45% to about 65% and that component II(A) have a DS of 2.1–2.5.

For the blends of the invention containing cellulose esters and/or aliphatic polyesters and/or aliphatic-aromatic copolyesters and/or polymeric compounds it is preferred that component III(B) is present in an amount of about 10% to about 50%, component III(A) is present in an amount of about 40% to about 88% and that component III(A) have a DS of 2.1–2.75, and that component III(C) is present in the amount of 2% to 10%. Also preferred is when component III(B) is present in an amount of about 2% to about 10%, component III(A) is present in an amount of about 40% to about 88% and that component III(A) have a DS of 2.1–2.75, and that component III(C) is present in the amount of 10% to 50%. Additionally preferred is when component III(B) is present in an amount of about 40% to about 88%, component III(A) is present in an amount of about 2% to about 10% and that component III(A) have a DS of 2.1–2.7, and that component III(C) is present in the amount of 10% to 50%. Also preferred is when component III(B) is present in an amount of about 10% to about 50%, component III(A) is present in an amount of about 2% to about 10% and that component III(A) have a DS of 2.1–2.7, and that component III(C) is present in the amount of 40% to 88%. Another preferred range is when component III(B) is present in an amount of about 20% to about 40%, component III(A) is present in an amount of about 20% to about 40% and that component III(A) have a DS of 2.1–2.7, and that component III(C) is present in the amount of 20% to 40%.

For the binary and ternary blends containing biodegradable additives it is preferred that component IV(B) is present in an amount of about 1% to about 10% and component IV(A) is present in an amount of about 90% to about 99%.

For the binary and ternary blends containing immiscible hydrophobic agents it is preferred that component V(B) is present in an amount of about 0.1% to about 1% and component V(A) is present in an amount of about 99% to about 99.9%.

Physical mixing of the components to form a blend can be accomplished in a number of ways such as mixing the components in the appropriate solvent (e.g., acetone, THF, $CH_2Cl_2$/MeOH, $CHCl_3$, dioxane, DMF, DMSO, AcOMe, AcOEt, pyridine) followed by film casting or fiber extrusion. The blend components can also be mixed by thermally compounding. The most preferred method is by thermally compounding in an apparatus such as a torque rheometer, a single screw extruder, or a twin screw extruder. The blends produced by thermally compounding can be converted to thin films by a number of methods known to those skilled in the art. For example, thin films can be formed by dipcoating as described in U.S. Pat. No. 4,372,311, by compression molding as described in U.S. Pat. No. 4,427,614, by melt extrusion as described in U.S. Pat. No. 4,880,592, by melt blowing, or by other similar methods. The blends can be converted to molded plastic objects by injection molding as well as by extrusion into a sheet from which an object is cut or stamped. The thermally compounded blends can be used for melt extrusion of fiber as well.

The fibers and films prepared from the blends and/or the AAPE of the present invention are useful in applications where protective barrier films are desirable. For example, they may be used in absorbent articles such as infant diapers, incontinence briefs (adult diapers), sanitary napkins, tampons, bed liners, bedpans, bandages, and the like. The biodegradable films, fibers, AAPE, and blends of the invention are particularly useful in disposable articles because of environmental considerations. The blends and/or films of the invention can also be used to make non-absorbent articles such as packaging materials (for example, foam sheets for packaging), food bags, trash bags, agricultural compost sheets, film base for tape and photographic film, as well as solid plastic articles such as syringes and camera cases.

Biodegradable materials, such as the preferred barrier films of this invention, are materials that are comprised of components which, by microbial catalyzed degradation, are reduced in film or fiber strength by reduction in polymer size to monomers or short chains which are then assimilated by the microbes. In an aerobic environment, these monomers or short chains are ultimately oxidized to $CO_2$, $H_2O$, and new cell biomass. In an anaerobic environment the monomers or short chains are ultimately oxidized to $CO_2$, $H_2$, acetate, methane, and cell biomass. Successful biodegradation requires that direct physical contact must be established between the biodegradable material and the active microbial population or the enzymes produced by the active microbial population. An active microbial population useful for degrading the films and blends of the invention can generally be obtained from any municipal or industrial wastewater treatment facility in which the influents (waste stream) are high in cellulose materials. Moreover, successful biodegradation requires that certain minimal physical and chemical requirements be met such as suitable pH, temperature, oxygen concentration, proper nutrients, and moisture level. We have found that certain cellulose esters are biodegradable in conventional wastewater treatment facilities and in an in vitro enrichment system and hence are particularly useful in the preparation of blends to be used for barrier films and fibers in disposable articles. We have also found that many of the blends and AAPE degrade in a composting environment and hence are useful in the preparation of materials to be used as environmentally nonpersistent materials.

The following examples are to illustrate the invention but should not be interpreted as a limitation thereon.

EXAMPLES

In the following examples, the blends were prepared by three general methods:

(i) the blend components are shaken together before compounding at the appropriate temperature in a Rheometrics Mechanical Spectrometer. The resulting resin is typically ground to 5 mm particle size and a portion is pressed between two metal plates at a temperature above the melt temperature of the resin to form a melt pressed film;

(ii) blends of the cellulose esters and polyesters were prepared by compounding on a 30 mm Werner-Pfleiderer twin screw extruder. The typical procedure is as follows: Two separate feed systems, one for the cellulosic and one for the polyester were utilized for this method of melt blending. The cellulose ester was added as a dry powder in Zone 1 and the polyester was added as a viscous liquid in Zone 3. The cellulose ester was added at the desired rate using an AccuRate feeder through a hopper into the barrel of the extruder. The polyester was pre-heated under nitrogen and was poured into a heated feed tank. The polyester was maintained under a nitrogen atmosphere and gravity fed through a stainless steel line to a gear pump which transferred the molten material through a stainless steel line (½ inch outer diameter) into the barrel of the extruder. All lines for this feed system were heated and insulated. The production rate of the extruder is in the range of 10–50 pounds/hr. The zone temperatures are set depending on the exact nature of the polyester and the cellulose ester and generally vary in the range of about 100° C. to 250° C. Afterwards, the two strands of material exiting the extruder were quenched in water and chopped with a CONAIR JETRO pelletizer.

(iii) blends of the cellulose esters and polyesters were prepared by compounding on a 30 mm Werner-Pfleiderer twin screw extruder. The typical procedure is as follows: A single feed system was utilized for this method of melt blending. The cellulose ester and the polyester were dry blended and added as a solid in Zone 1. The dry blend was added at the desired rate using an AccuRate feeder through a hopper into the barrel of the extruder. The production rate of the extruder is in the range of 10–50 pounds/hr. The zone temperatures are set depending on the exact nature of the polyester and the cellulose ester and generally vary in the range of about 100° C. to 250° C. Afterwards, the two strands of material exiting the extruder were quenched in water and chopped with a CONAIR JETRO pelletizer.

The tensile strength, break to elongation, and tangent modulus of the films are measured by ASTM method D882; the tear force is measured by ASTM method D1938; the oxygen and water vapor transmission rates are measured by ASTM methods D3985 and F372, respectively. The tensile strength and elongation at break for molded pieces are measured by ASTM method D638; the flexural strength and modulus by ASTM method D790; the Izod impact strength by ASTM method D256; the heat deflection temperature by ASTM method D648. Inherent viscosities are measured at a temperature of 25° C. for a 0.5 gram sample in 100 ml of a 60/40 by weight solution of phenol/tetrachloroethane. Dynamic mechanical thermal analysis (DMTA) spectra were collected using a Polymer Laboratories Mk II at 4° C./min and 1 Hz.

Abbreviations used herein are as follows: "IV" is inherent viscosity; "g" is gram; "psi" is pounds per square inch; "cc" is cubic centimeter; "m" is meter; "rpm" is revolutions per minute; "DSPr" is degree of substitution per anhydroglucose unit for propionyl; "DSAC" is degree of substitution per anhydroglucose unit for acetyl; "DSBu" is degree of substitution per anhydroglucose unit for butyryl; "BOD" is biochemical oxygen demand; "vol." or "v" is volume; "wt." is weight; "mm" is micrometer; "NaOAc" is sodium acetate; "nm" is not measured; "CE" is cellulose ester; "PE" is polyester; "DOA" is dioctyl adipate; "HDT" is heat deflection temperature; "WVTR" is water vapor transmission rate; "mil" is 0.001 inch. Relative to the clarity of the films, "+" indicates a transparent film characteristic of a miscible blend; "±" indicates a hazy film characteristic of a partially miscible film; "−" indicates an opaque film characteristic of a immiscible blend; "AAPE" is aliphatic-aromatic copolyester and, as used herein, refers to the copolyesters where blending is not required. Relative to naming of the cellulose ester, "CAP" is cellulose acetate propionate; "CA" is cellulose acetate; "CAB" is cellulose acetate butyrate. Relative to naming of the polyester, representative examples are: "PTS(T) [85/15]" is poly(tetramethylene succinate-co-terephthalate) were the mole per cent of succinate to terephthalate is 85/15; "PTA(T) [85/15]" is poly(tetramethylene adipate-co-terephthalate) were the mole per cent of adipate to terephthalate is 85/15; "PTG(T) [85/15]" is poly(tetramethylene glutarate-co-terephthalate) were the mole per cent of glutarate to terephthalate is 85/15; "PTG(T)(D) [60/35/5]" is poly(tetramethylene glutarate-co-terephthalate-co-diglycolate) were the mole per cent of glutarate to terephthalate to diglycolate is 60/35/5; "PTG(N) [85/15]" is poly(tetramethylene glutarate-co-naphthalate) were the mole per cent of glutarate to naphthalate is 85/15; "PES" is poly(ethylene succinate); "PHS" is poly(hexamethylene succinate); "PEG" is poly(ethylene glutarate); "PTG" is poly(tetramethylene glutarate); "PHG" is poly(hexamethylene glutarate); "PT(E)G [50/50]" is poly(tetramethylene-co-ethylene glutarate) were the mole % of tetramethylene to ethylene is 50/50; "PEA" is poly(ethylene adipate); "PDEA" is poly(diethylene adipate); "PHA" is poly(hexamethylene adipate). Other abbreviations are: "TEGDA" is triethylene glycol diacetate; "PVA" is poly(vinyl acetate); "PMMA" is poly(methyl methacrylate); "PEMA" is poly(ethyl methacrylate). MYVAPLEX 600 is the trade name for concentrated glyceryl monostearates and is available from Eastman Chemical Company. MYVAPLEX concentrated glyceryl monostearate is a 90% minimum distilled monoglyceride produced from hydrogenated soybean oil which is composed primarily of stearic acid esters. MYVACET is the trade name for distilled acetylated monoglycerides of modified fats. The per cent acetylation of MYVACET 507 ranges from 48.5 to 51.5; the per cent acetylation of MYVACET 707 ranges from 66.5 to 69.5; the per cent acetylation of MYVACET 908 is a minimum of 96.

MYVEROL is the trade name for concentrated glyceryl monostearates and is available from Eastman Chemical Company. MYVEROL is very similar to MYVAPLEX except that the distilled monoglyceride is produced from different fat sources.

Example 1

Blends of cellulose acetate propionate (DSAC=0.10, $DS_{Pr}$=2.64, IV=1.3) and aliphatic-aromatic copolyesters and films made from the blends were prepared using the standard procedures. Glass transition temperature were measured by DMTA and were calculated using the Fox-Flory equation. The results are given in Tables I and II.

TABLE I

Tg, IV, and Clarity of CAP/Aliphatic-Aromatic Copolyester Blends

| Entry | Polyester | Tg (exp) ° C. | Tg (cal) ° C. | IV PE | IV Blend | Clarity |
|---|---|---|---|---|---|---|
| 1 | 20% PTS(T) [85/15] | 124 | 110 | 1.0 | 1.1 | + |
| 2 | 40% PTS(T) [85/15] | 93 | 75 | 1.0 | 1.1 | + |
| 3 | 20% PTA(T) [85/15] | 125 | 110 | 0.7 | 1.0 | + |
| 4 | 40% PTA(T) [85/15] | 87 | 76 | 0.7 | 0.9 | + |
| 5 | 20% PEG(T) [85/15] | 139 | 110 | 0.6 | 0.9 | + |
| 6 | 40% PEG(T) [85/15] | 75 | 78 | 0.6 | 1.0 | + |
| 7 | 10% PEG(T) [70/30] | 146 | 143 | 0.9 | 1.0 | + |
| 8 | 20% PEG(T) [70/30] | 136 | 113 | 0.9 | 1.0 | + |
| 9 | 30% PEG(T) [70/30] | 126* | 97 | 0.9 | 1.0 | + |
| 10 | 40% PEG(T) [70/30] | 82 | 83 | 0.6 | 1.0 | + |
| 11 | 55% PEG(T) [70/30] | 62 | 59 | 0.6 | 0.9 | + |
| 12 | 70% PEG(T) [70/30] | 25,85,98 | 34 | 0.9 | 0.9 | + |
| 13 | 40% PTG(T) [95/5] | 93 | 66 | 1.2 | nm | + |
| 14 | 20% PTG(T) [90/10] | 127 | 105 | 0.9 | nm | + |
| 15 | 40% PTG(T) [90/10] | 88 | 65 | 0.9 | 1.0 | + |
| 16 | 40% PT(E)G(T) [50/50,85/15] | 71 | 72 | 0.7 | 1.0 | + |
| 17 | 20% PT(E)G(T) [50/50,70/30] | 125 | 110 | 0.7 | 1.0 | + |
| 18 | 40% PT(E)G(T) [50/50,70/30] | 76 | 77 | 0.7 | 1.0 | + |
| 19 | 40% PTG(T) [85/15] | 75 | 71 | 0.7 | 1.0 | + |
| 20 | 20% PTG(T) [70/30] | 135 | 110 | 0.7 | 1.0 | + |
| 21 | 40% PTG(T) [70/30] | 82 | 73 | 0.7 | 1.0 | + |
| 22 | 20% PTG(T) [60/40] | 143 | 113 | 1.5 | 1.1 | + |
| 23 | 40% PTG(T) [60/40] | 130* | 78 | 1.5 | 1.2 | + |
| 24 | 60% PTG(T) [60/40] | 3,76,112 | 43 | 1.5 | 1.0 | ± |
| 25 | 70% PTG(T) [60/40] | 2, 108 | 26 | 1.5 | 1.2 | ± |
| 26 | 80% PTG(T) [60/40] | 5 | 9 | 1.5 | 0.9 | ± |
| 27 | 20% PHG(T) [80/20] | 143 | 106 | 1.2 | 1.2 | + |
| 28 | 40% PHG(T) [80/20] | 105* | 66 | 0.7 | 0.9 | + |
| 29 | 20% PEG(N) [85/15] | 138 | 111 | 0.8 | 1.0 | + |
| 30 | 40% PEG(N) [65/15] | 102* | 77 | 0.8 | 0.9 | + |

*Broad transitions with shoulders.

TABLE II

Mechanical Properties, Tear Strength, and Water Vapor Transmission Rates Of Cellulose Eeter/Aliphatic-Aromatic Copolyester Blends

| Sample | Polyester | Elongation at Break (%) | Tangent Modulus ($10^5$ psi) | Tensile Strength ($10^3$ psi) | Tear Strength (g/mil) | WVTR (g mil/100) in$^2$-24 hours) |
|---|---|---|---|---|---|---|
| 1  | 20% PTS(T) [85/15]         | 8   | 2.11 | 5.97 | 14.8 | 222 |
| 2  | 40% PTS(T) [85/15]         | 82  | 0.22 | 2.83 | 14.7 | 173 |
| 3  | 20% PTA(T) [85/15]         | 6   | 1.86 | 5.03 | 12.0 | nm  |
| 4  | 40% PTA(T) [85/15]         | 61  | 0.19 | 1.62 | 10.3 | nm  |
| 5  | 20% PEG(T) [85/15]         | 4   | 2.21 | 6.11 | 8.0  | nm  |
| 6  | 40% PEG(T) [85/15]         | 91  | 0.31 | 2.89 | 14.4 | 253 |
| 7  | 10% PEG(T) [70/30]         | 3   | 2.21 | 4.90 | 10.0 | 172 |
| 8  | 20% PEG(T) [70/30]         | 4   | 2.21 | 6.29 | 7.5  | 216 |
| 9  | 30% PEG(T) [70/30]         | 18  | 1.35 | 4.24 | 11.5 | 184 |
| 10 | 40% PEG(T) [70/30]         | 47  | 0.59 | 2.83 | 10.9 | 145 |
| 11 | 55% PEG(T) [70/30]         | 54  | 0.06 | 1.16 | 12.6 | 272 |
| 12 | 70% PEG(T) [70/30]         | 114 | 0.02 | 0.42 | 25.8 | nm  |
| 13 | 40% PTG(T) [95/5]          | 75  | 0.10 | 1.70 | 9.3  | nm  |
| 14 | 20% PTG(T) [90/10]         | 21  | 1.78 | 5.33 | 11.4 | nm  |
| 15 | 40% PTG(T) [90/10]         | 77  | 0.12 | 2.02 | 9.9  | nm  |
| 16 | 40% PT(E)G(T) [50/50,85/15]| 81  | 0.27 | 2.58 | 14.1 | 216 |
| 17 | 20% PT(E)G(T) [50/50,70/30]| 3   | 2.15 | 5.58 | 7.2  | nm  |
| 18 | 40% PT(E)G(T) [50/50,70/30]| 61  | 0.43 | 2.81 | 13.7 | 175 |
| 19 | 40% PTG(T) [85/15]         | 83  | 0.24 | 2.48 | 11.5 | 246 |
| 20 | 20% PTG(T) [70/30]         | 5   | 1.23 | 6.26 | 12.4 | 188 |
| 21 | 40% PTG(T) [70/30]         | 50  | 0.37 | 2.05 | 16.3 | 238 |
| 22 | 20% PTG(T) [60/40]         | 8   | 1.13 | 3.47 | 20.2 | 364 |
| 23 | 40% PTG(T) [60/40]         | 82  | 0.99 | 4.01 | 23.6 | 275 |
| 24 | 60% PTG(T) [60/40]         | 72  | 0.28 | 1.89 | 14.9 | nm  |
| 25 | 70% PTG(T) [60/40]         | 63  | 0.21 | 1.32 | 19.1 | nm  |
| 26 | 80% PTG(T) [60/40]         | 207 | 0.09 | 1.11 | 59.2 | nm  |
| 27 | 20% PHG(T) [80/20]         | 30  | 1.5  | 4.87 | 4.6  | nm  |
| 28 | 40% PHG(T) [80/20]         | 45  | 0.25 | 1.35 | 10.5 | nm  |
| 29 | 20% PEG(N) [85/15]         | 12  | 2.14 | 6.05 | 11.1 | 175 |
| 30 | 40% PEG(N) [85/15]         | 69  | 0.38 | 2.66 | 14.4 | 308 |

The IV data from Table I illustrates that the molecular weight of the blend components are preserved in the blending process. As the clarity indicates, the films were transparent which is characteristic of miscible blends.

Table I demonstrates that each of the blends involving 20% aliphatic-aromatic copolyester (entries 1, 3, 5, 8, 14, 17, 20, 22, 27, and 29) had an experimental $Tg_{12}$ which was 14 to 37° C. higher than the $Tg_{12}$ calculated for each blend. The 40% aliphatic-aromatic copolyester blends involving a C4 diacid (entry 2), a C6 diacid (entry 4), or a C10 aromatic diacid (entry 30) also showed a 18, 11, and 25° C., respectively, positive deviation of the experimental $Tg_{12}$ from the theoretical $Tg_{12}$. Within the family of 40% aliphatic-aromatic copolyester involving a Cs aliphatic diacid, the experimental $Tg_{12}$ of entries 6, 10, 16, 19, and 21 (15–30% C6 aromatic diacid) showed good agreement with the theoretical $Tg_{12}$ (±10° C.). In contrast, the experimental Tg12's of the 40% PTG(T) blends containing 5, 10, and 40% C6 aromatic diacid showed a 27, 23, and 52° C., respectively, positive deviation from the calculated value. In the series of 10–70% PEG(T) [70/30] (entries 7–12), the 10–30% blends showed a positive deviation of the experimental $T_{12}$ from the calculated values, the 40–55% blends had $Tg_{12}$'s which showed excellent agreement with the calculated $Tg_{12}$'s, and the 70% blend showed multiple Tg's characteristic of a partially miscible blend. In contrast, the series of 20–70% PTG(T) [60/40] blends (entries 22–25) either had multiple $Tg_{12}$'s or $Tg_{12}$'s that were quite different from theoretical. At very high levels of aliphatic-aromatic copolyester (cf. entry 26), single Tg's were observed. Analysis of this type suggests that blends of cellulose esters with aliphatic-aromatic copolyester involving a C5 aliphatic diacid are generally miscible in approximately the 30–55% range when the aromatic portion of the copolyesters is approximately 15–30%. Aliphatic-aromatic copolyester blends involving a C5 aliphatic diacid outside of the 30–55% range exhibit varying levels of miscibilities. Blends involving other aliphatic diacids also exhibit varying levels of miscibilities through a wider range.

Blend miscibility is also strongly dependent upon the molecular weight of the polyester. In general, a low I.V. polyester will give a wider window of miscibility.

Cellulose esters typically have high WVTR (>500 g mil/100 in$^2$-24 h). As Table II shows, all of the CAP/aliphatic-aromatic copolyester blends have WVTR less than 500 g mil/100 in2-24 h. Table II also demonstrates that a wide range of physical properties for materials prepared from the blends are possible depending upon the blend components and blend composition. Many of the aliphatic-aromatic copolyester blends gave unexpected and unusual physical properties. For example, the tangent modulus (Table II) for the 20% blends were, for the most part, surprisingly high relative to the CAP ($2.1 \times 10^5$ psi). With the exception of the blends involving PTG(T) [70/30] and PTG(T) [60/40], the tangent moduli all remained above $1.5 \times 10^5$ psi. Even more surprising was the tensile strength for the 20% blends. With the exception of the PTG(T) [60/40] blend, the tensile strength of these blends were all above $5.0 \times 10^3$ psi; in some cases the tensile strength was improved relative to the CAP ($5.5 \times 10^3$). In general, with the exception of the PTG(T) [60/40] blends, all of the blends involving 20% aliphatic-aromatic copolyester behaved very similar to the blend major component, cellulose acetate propionate. In effect, we were able to substitute 20% of a copolyester, which generally has much different physical properties than the cellulose ester blend component, for cellulose ester without lowering, and in some case improving, the mechanical properties inherent to the cellulose acetate propionate.

Example 2

Blends of cellulose esters and succinate polyesters and films therefrom were prepared using the standard procedures. The results are given in Tables III and IV.

TABLE III

DS/AGU, IV, and Clarity of Cellulose Ester/Polyester Blends: C4 Diacids

| Entry | Polyester | $Ds_{Ac}$ | $Ds_{Pr}$ | $DS_{Bu}$ | IV CE | IV PE | IV Blend | Clarity |
|---|---|---|---|---|---|---|---|---|
| 31 | 10% PES | 2.50 | — | — | 1.2 | 1.0 | 1.25 | + |
| 32 | 20% PES | 2.50 | — | — | 1.2 | 1.0 | 1.18 | + |
| 33 | 20% PES | 0.10 | 2.64 | — | 1.3 | 1.1 | 1.18 | + |
| 34 | 40% PES | 0.10 | 2.64 | — | 1.3 | 1.0 | 1.11 | + |
| 35 | 20% PHS | 0.10 | 2.64 | — | 1.3 | 1.0 | 1.16 | + |
| 36 | 40% PHS | 0.10 | 2.64 | — | 1.3 | 1.0 | 1.11 | + |

TABLE IV

Mechanical Properties and Tear Strength of Films Prepared From Cellulose Ester/Polyester Blends: C4 Diacids

| Entry | Polyester | Elongation at Break (%) | Tangent Modulus ($10^5$ psi) | Tensile Strength ($10^3$ psi) | Tear Strength (g/mil) |
|---|---|---|---|---|---|
| 31 | 10% PES | nm | nm | nm | nm |
| 32 | 20% PES | nm | nm | nm | nm |
| 33 | 20% PES | 11 | 1.92 | 5.45 | nm |
| 34 | 40% PES | 48 | 0.71 | 2.97 | nm |
| 35 | 20% PHS | 36 | 1.70 | 4.68 | nm |
| 36 | 40% PHS | 87 | 0.26 | 2.32 | 12.2 |

The IV data from Table III illustrates that the molecular weight of the blend components are preserved in the blending process. As the clarity indicates, the films were transparent which is characteristic of miscible blends. Furthermore, the Tg of the blend was measured for representative samples. Entries 34 and 36 had a single Tg of 80° C. and 70° C., respectively. A single Tg is also characteristic of miscible blends. As Table IV demonstrates, a very wide range of physical properties for materials prepared from the blends are possible by proper selection of the blend composition.

Example 3

Blends of cellulose esters and glutarate polyesters and films therefrom were prepared using the standard procedures. The results are given in Tables V and VI.

TABLE V

DS/AGU, IV, and Clarity of Cellulose Ester/Polyester Blends: C5 Diacids

| Entry | Polyester | $Ds_{Ac}$ | $Ds_{Pr}$ | $DS_{Bu}$ | IV CE | IV PE | IV Blend | Clarity |
|---|---|---|---|---|---|---|---|---|
| 37 | 50% PEG | 2.50 | — | — | 1.2 | — | nm | + |
| 38 | 20% PEG | 0.10 | 2.64 | — | 1.3 | 1.2 | 1.21 | + |
| 39 | 40% PEG | 0.10 | 2.64 | — | 1.3 | 1.2 | 1.19 | + |
| 40 | 35% PEG | 0.34 | 2.15 | — | 1.6 | 0.9 | nm | + |
| 41 | 40% PEG | 0.34 | 2.15 | — | 1.6 | 0.9 | nm | + |
| 42 | 45% PEG | 0.34 | 2.15 | — | 1.6 | 0.9 | nm | + |
| 43 | 35% PEG | 0.12 | 2.14 | — | 1.3 | 1.1 | nm | + |
| 44 | 40% PEG | 0.12 | 2.14 | — | 1.3 | 0.9 | nm | + |
| 45 | 35% PEG | 0.11 | 2.05 | — | 1.6 | 0.9 | nm | + |
| 46 | 40% PEG | 0.11 | 2.05 | — | 1.6 | 0.9 | nm | + |
| 47 | 45% PEG | 0.11 | 2.05 | — | 1.6 | 0.9 | nm | + |
| 48 | 20% PDEG | 0.10 | 2.64 | — | 1.3 | 1.1 | 1.21 | + |
| 49 | 40% PDEG | 0.10 | 2.64 | — | 1.3 | 1.1 | nm | + |
| 50 | 40% PT(E)G [50,50] | 0.10 | 2.64 | — | 1.3 | 0.7 | nm | + |
| 51 | 10% PTG | 0.10 | 2.64 | — | 1.3 | 0.5 | 1.20 | + |
| 52 | 20% PTG | 0.10 | 2.64 | — | 1.3 | 0.5 | 1.21 | + |
| 53 | 30% PTG | 0.10 | 2.64 | — | 1.3 | 0.6 | 1.07 | + |
| 54 | 35% PTG | 0.10 | 2.64 | — | 1.3 | 0.5 | 1.07 | + |
| 55 | 40% PTG | 0.10 | 2.64 | — | 1.3 | 0.5 | 1.11 | + |
| 56 | 40% PTG | 0.10 | 2.64 | — | 1.3 | 0.6 | 1.06 | + |
| 57 | 40% PTG | 0.10 | 2.64 | — | 1.3 | 1.1 | nm | + |
| 58 | 20% PTG | 0.10 | 2.64 | — | 1.3 | 1.7 | 1.25 | + |
| 59 | 25% PTG | 0.10 | 2.64 | — | 1.3 | 1.7 | 1.27 | + |
| 60 | 30% PTG | 0.10 | 2.64 | — | 1.3 | 1.7 | 1.25 | + |
| 61 | 35% PTG | 0.10 | 2.64 | — | 1.3 | 1.7 | 1.25 | + |
| 62 | 40% PTG | 0.10 | 2.64 | — | 1.3 | 1.7 | 1.31 | + |
| 63 | 50% PTG | 0.10 | 2.64 | — | 1.3 | 1.7 | 1.30 | + |
| 64 | 40% PTG | 0.17 | 2.29 | — | 1.7 | 1.1 | nm | + |
| 65 | 40% PTG | 0.04 | 2.28 | — | 1.6 | 1.7 | nm | + |
| 66 | 40% PTG | 0.34 | 2.15 | — | 1.6 | 1.1 | nm | + |
| 67 | 35% PTG | 0.34 | 2.15 | — | 1.6 | 1.1 | nm | + |
| 68 | 40% PTG | 0.10 | 2.16 | — | 1.0 | 1.1 | nm | + |
| 69 | 40% PTG | 0.12 | 2.14 | — | 1.3 | 1.1 | nm | + |
| 70 | 35% PTG | 0.11 | 2.05 | — | 1.6 | 1.1 | nm | + |
| 71 | 40% PTG | 0.11 | 2.05 | — | 1.6 | 1.1 | nm | + |
| 72 | 45% PTG | 0.11 | 2.05 | — | 1.6 | 1.1 | nm | + |
| 73 | 30% PHG | 0.10 | 2.64 | — | 1.3 | 0.5 | 1.06 | + |
| 74 | 40% PHG | 0.10 | 2.64 | — | 1.3 | 0.5 | 0.99 | + |
| 75 | 35% PTG | 1.01 | — | 1.67 | 1.2 | — | nm | + |
| 76 | 40% PTG | 2.04 | — | 0.70 | 1.2 | — | nm | + |

TABLE VI

Mechanical Properties and Tear Strength for Films Prepared From Cellulose Ester/Aliphatic Polyester Blends: C5 Diacids

| Entry | Polyester | Elongation at Break (%) | Tangent Modulus ($10^5$ psi) | Tensile Strength ($10^3$ psi) | Tear Strength (g/mil) |
|---|---|---|---|---|---|
| 37 | 50% PEG | nm | nm | nm | nm |
| 38 | 20% PEG | 30 | 1.60 | 4.79 | nm |
| 39 | 40% PEG | 95 | 0.24 | 2.49 | 13.3 |
| 40 | 35% PEG | 80 | 0.52 | 3.44 | 18.5 |
| 41 | 40% PEG | 84 | 0.33 | 2.78 | 10.0 |
| 42 | 45% PEG | 104 | 0.21 | 2.56 | 15.9 |
| 43 | 35% PEG | 33 | 0.38 | 1.80 | 12.6 |
| 44 | 40% PEG | 19 | 0.24 | 1.07 | 9.8 |
| 45 | 35% PEG | 51 | 0.48 | 3.04 | 13.3 |
| 46 | 40% PEG | 86 | 0.32 | 2.80 | 10.4 |
| 47 | 45% PEG | 77 | 0.20 | 1.61 | 12.7 |
| 48 | 20% PDEG | 24 | 1.41 | 3.54 | 5.1 |
| 49 | 40% PDEG | 60 | 0.14 | 1.08 | 19.8 |
| 50 | 40% PT(E)G [50,50] | 76 | 0.15 | 1.73 | 9.1 |
| 51 | 10% PTG | 30 | 1.70 | 5.49 | 12.7 |
| 52 | 20% PTG | 43 | 1.20 | 3.72 | nm |
| 53 | 30% PTG | 65 | 0.73 | 2.97 | 16.7 |
| 54 | 35% PTG | 88 | 0.25 | 2.54 | 14.9 |
| 55 | 40% PTG | 53 | 0.15 | 1.18 | 11.8 |
| 56 | 40% PTG | 61 | 0.13 | 1.26 | 12.4 |
| 57 | 40% PTG | 71 | 0.12 | 1.59 | 13.3 |
| 58 | 20% PTG | 18 | 1.68 | 4.64 | 12.5 |
| 59 | 25% PTG | 67 | 1.27 | 4.41 | 18.7 |
| 60 | 30% PTG | 69 | 0.96 | 3.31 | 21.5 |
| 61 | 35% PTG | 72 | 0.45 | 2.36 | 22.9 |

TABLE VI-continued

Mechanical Properties and Tear Strength for Films Prepared From Cellulose Ester/Aliphatic Polyester Blends: C5 Diacids

| Entry | Polyester | Elongation at Break (%) | Tangent Modulus ($10^5$ psi) | Tensile Strength ($10^3$ psi) | Tear Strength (g/mil) |
|---|---|---|---|---|---|
| 62 | 40% PTG | 128 | 0.13 | 2.68 | 18.0 |
| 63 | 50% PTG | 117 | 0.05 | 2.14 | 23.0 |
| 64 | 40% PTG | 113 | 0.22 | 2.67 | 15.8 |
| 65 | 40% PTG | 42 | 0.21 | 1.29 | nm |
| 66 | 40% PTG | 97 | 0.27 | 2.50 | 19.9 |
| 67 | 35% PTG | 92 | 0.59 | 3.94 | 19.8 |
| 68 | 40% PTG | 37 | 0.16 | 1.09 | 12.2 |
| 69 | 40% PTG | 36 | 0.22 | 1.27 | 15.4 |
| 70 | 35% PTG | 54 | 0.43 | 2.45 | 12.8 |
| 71 | 40% PTG | 53 | 0.26 | 1.97 | 12.9 |
| 72 | 45% PTG | 47 | 0.19 | 1.32 | 9.3 |
| 73 | 30% PHG | 57 | 0.68 | 2.43 | 17.4 |
| 74 | 40% PHG | 60 | 0.16 | 1.23 | 12.4 |
| 75 | 35% PTG | 93 | 0.32 | 2.99 | 12.4 |
| 76 | 40% PTG | 27 | 0.86 | 0.35 | 12.6 |

The IV data from Table V illustrate that the molecular weight of the blend components are preserved in the blending process. As the clarity indicates, the films were transparent which is characteristic of miscible blends. Furthermore, the Tg of the blend was measured for representative samples. Entries 37, 49, 51, 54, 55, 59, and 74 had a single Tg of 120, 70, 125, 72, 66, 108, and 70° C., respectively. A single Tg is also characteristic of miscible blends. As Table VI demonstrates, a very wide range of physical properties for materials prepared from the blends are possible by proper selection of the blend composition.

Example 4

Blends of cellulose esters and adipate polyesters and films therefrom were prepared using the standard procedures. The results are given in Tables VII and VIII.

TABLE VII

DS/AGU, IV, And Clarity of Cellulose Ester/Aliphatic Polyeater Blends: C6 Diacids

| Entry | Polyester | $DS_{Ac}$ | $DS_{Pr}$ | $DS_{Bu}$ | IV CE | IV PE | IV Blend | Clarity |
|---|---|---|---|---|---|---|---|---|
| 77 | 20% PEA | 0.10 | 2.64 | — | 1.3 | 0.6 | 1.16 | + |
| 78 | 25% PEA | 0.10 | 2.64 | — | 1.3 | 0.6 | 1.11 | + |
| 79 | 30% PEA | 0.10 | 2.64 | — | 1.3 | 0.6 | 1.08 | + |
| 80 | 35% PEA | 0.10 | 2.64 | — | 1.3 | 0.6 | 1.04 | + |
| 81 | 40% PEA | 0.10 | 2.64 | — | 1.3 | 0.6 | 1.00 | + |
| 82 | 45% PEA | 0.10 | 2.64 | — | 1.3 | 0.6 | 0.96 | + |
| 83 | 50% PEA | 0.10 | 2.64 | — | 1.3 | 0.6 | 0.92 | + |
| 84 | 20% PDEA | 0.10 | 2.64 | — | 1.3 | 0.7 | 1.15 | + |
| 85 | 40% PDEA | 0.10 | 2.64 | — | 1.3 | 0.7 | 1.11 | + |
| 86 | 20% PHA | 0.10 | 2.64 | — | 1.3 | 0.7 | 1.17 | + |
| 87 | 40% PRA | 0.10 | 2.64 | — | 1.3 | 0.5 | 1.05 | + |

TABLE VIII

Mechanical Properties and Tear Properties of Films Prepared From Cellulose Ester/Polyester Blends: C6 Diacids

| Entry | Polyester | Elongation at Break (%) | Tangent Modulus ($10^5$ psi) | Tensile Strength ($10^3$ psi) | Tear Strength (g/mil) |
|---|---|---|---|---|---|
| 77 | 20% PEA | 13 | 1.39 | 3.95 | 4.1 |
| 78 | 25% PEA | 43 | 0.99 | 3.37 | 14.1 |
| 79 | 30% PEA | 74 | 0.57 | 2.76 | 16.6 |
| 80 | 35% PEA | 90 | 0.32 | 2.44 | 12.6 |
| 81 | 40% PEA | 75 | 0.14 | 1.37 | 13.0 |
| 82 | 45% PEA | 62 | 0.06 | 1.20 | 4.1 |
| 83 | 50% PEA | 75 | 0.03 | 1.03 | 4.7 |
| 84 | 20% PDEA | 24 | 1.46 | 4.05 | 6.0 |
| 85 | 40% PDEA | 64 | 0.12 | 1.11 | 13.3 |
| 86 | 20% PHA | 18 | 1.30 | 3.60 | 15.2 |
| 87 | 40% PHA | 81 | 0.14 | 1.36 | 13.6 |

The IV data from Table VII illustrate that the molecular weight of the blend components are preserved in the blending process. As the clarity indicates, the films were transparent which is characteristic of miscible blends. Furthermore, the Tg of the blend was measured for representative samples. Entries 80 and 84 had a single Tg of 78 and 130° C., respectively. A single Tg is also characteristic of miscible blends. As Table VIII demonstrates, a very wide range of physical properties for materials prepared from the blends are possible by proper selection of the blend composition.

Example 5

Blends of cellulose esters and aliphatic polyesters containing different additives and films therefrom were prepared using the standard procedures. The film of entries 96–101, 104, and 105 are blown film where T means transverse direction and M means machine direction. The results are given in Tables IX and X.

TABLE IX

DS/AGU, IV, Clarity of Cellulose Ester/Aliphatic Polyester Blends Containing Representative Additives

| Entry | Polyester/Additive | $DS_{Ac}$ | $DS_{Pr}$ | $DS_{Bu}$ | IV CE | IV PE | Clarity |
|---|---|---|---|---|---|---|---|
| 88 | 39.9% PTG 0.1% Iron Stearate | 0.10 | 2.64 | — | 1.3 | 1.1 | + |
| 89 | 39.9% PTG 0.1% Zinc Stearate | 0.10 | 2.64 | — | 1.3 | 1.1 | + |
| 90 | 39.9% PTG 0.1% Mg Octanoate | 0.10 | 2.64 | — | 1.3 | 1.1 | + |
| 91 | 39.9% PTG 0.1% CaCO$_3$ | 0.10 | 2.64 | — | 1.3 | 1.1 | + |
| 92 | 39% PTG 1% CaCO$_3$ | 0.10 | 2.64 | — | 1.3 | 1.1 | + |
| 93 | 37.5% PTG 2.5% CaCO$_3$ | 0.10 | 2.64 | — | 1.3 | 1.1 | 1 |
| 94 | 39.75% 0.25% Zeolite | 0.10 | 2.64 | — | 1.3 | 1.1 | + |
| 95 | 39% PTG 1% Zeolite | 0.10 | 2.64 | — | 1.3 | 1.1 | + |
| 96 | 40% PTG$^M$ 1% Microcrystalline Cellulose | 0.10 | 2.64 | — | 1.3 | 1.1 | + |
| 97 | 40% PTG$^T$ 1% Microcrystalline Cellulose | 0.10 | 2.64 | — | 1.3 | 1.1 | + |
| 98 | 40% PTG$^M$ 2% Microcrystalline Cellulose | 0.10 | 2.64 | — | 1.3 | 1.1 | + |
| 99 | 40% PTG$^T$ 2% Microcrystalline | 0.10 | 2.64 | — | 1.3 | 1.1 | + |

TABLE IX-continued

DS/AGU, IV, Clarity of Cellulose Ester/Aliphatic Polyester Blends Containing Representative Additives

| Entry | Polyester/Additive | $DS_{Ac}$ | $DS_{Pr}$ | $DS_{Bu}$ | IV CE | IV PE | Clarity |
|---|---|---|---|---|---|---|---|
| 100 | Cellulose 40% PTG$^M$ 1% Microcrystalline Cellulose, 1% Silica, 1% TiO$_2$ | 0.10 | 2.64 | — | 1.3 | 1.1 | 1 |
| 101 | 40% PTG$^T$ 1% Microcrystalline Cellulose, 1% Silica, 1% TiO$_2$ | 0.10 | 2.64 | — | 1.3 | 1.1 | 1 |
| 102 | 20% PTG 10% TEGDA | 0.10 | 2.64 | — | 1.3 | 1.7 | + |
| 103 | 40% PTG 2.5% Cellulose Monoacetate, 0.5% MYVAPLEX 600 | 0.10 | 2.64 | — | 1.3 | 1.1 | + |
| 104 | 41% PTG$^M$ 0.5% PBT dye, 2% TiO$_2$, 1% MYVAPLEX 600 | 0.10 | 2.64 | — | 1.0 | nm | 1 |
| 105 | 41% PTG$^T$ 0.5% PBT dye, 2% TiO$_2$, 1% MYVAPLEX 600 | 0.10 | 2.64 | — | 1.0 | nm | 1 |

$^1$Films were opaque or colored due to the additive.

TABLE X

Mechanical Properties and Tear Strength of Films Prepared From Cellulose Ester/Polyester Blends Containing Representative Additives

| Entry | Polyester/Additive | Elongation at Break (%) | Tangent Modulus ($10^5$ psi) | Tensile Strength ($10^3$ psi) | Tear Strength (g/mil) |
|---|---|---|---|---|---|
| 88 | 39.9% PTG 0.1% Iron Stearate | 83 | 0.18 | 2.22 | 10.8 |
| 89 | 39.9% PTG 0.1% Zinc Stearate | 68 | 0.14 | 1.70 | 11.1 |
| 90 | 39.9% PTG 0.1% Mg Octanoate | 74 | 0.14 | 1.97 | 11.5 |
| 91 | 39.9% PTG 0.1% CaCO$_3$ | 56 | 0.12 | 1.42 | 12.7 |
| 92 | 39% PTG 1% CaCO$_3$ | 51 | 0.11 | 1.17 | 13.2 |
| 93 | 37.5% PTG 2.5% CaCO$_3$ | 52 | 0.19 | 1.38 | 14.2 |
| 94 | 39.75% PTG 0.25% Zeolite | 64 | 0.08 | 1.67 | 12.8 |
| 95 | 39% PTG 1% Zeolite | 52 | 0.13 | 1.27 | 12.4 |
| 96 | 40% PTG$^M$ 1% Microcrystalline Cellulose | 67 | 0.27 | 2.46 | 7.0 |
| 97 | 40% PTG$^T$ 1% Microcryatalline Cellulose | 36 | 0.30 | 1.09 | 6.8 |
| 98 | 40% PTG$^M$ 2% Microcrytalline Cellulose | 43 | 0.22 | 1.56 | 7.1 |
| 99 | 40% PTG$^T$ 2% Microcryatalline Cellulose | 59 | 0.27 | 1.89 | 6.8 |
| 100 | 40% PTG$^M$ 1% Microcrystalline Cellulose, 1% Silica, 1% TiO$_2$ | 65 | 0.37 | 2.11 | 7.9 |
| 101 | 40% PTG$^T$ 1% Microcrystalline Cellulose, 1% Silica, 1% TiO$_2$ | 48 | 0.24 | 1.76 | 8.3 |
| 102 | 20% PTG 10% TEGDA | 79 | 0.42 | 1.87 | 12.7 |
| 103 | 40% PTG 2.5% Cellulose Monoacetate, 0.5% MYVAPLEX 600 | 56 | 0.14 | 1.06 | 13.7 |
| 104 | 41% PTG$^M$ 0.5% PTT dye, 2% TiO$_2$, 1% MYVAPLEX 600 | 80 | 0.17 | 3.40 | 10.0 |
| 105 | 41% PTG$^T$ 0.5% PTT dye, 2% TiO$_2$, 1% MYVAPLEX 600 | 68 | 0.30 | 4.48 | 7.5 |

As Table IX demonstrates, the blends of this invention can contain many different types of additives ranging from pro-oxidants (cf. entries 88–90), inorganics (cf. entries 91–95, 104,105), organic additives which are highly biodegradable (cf. 96–101, 103), polymer dyes and pigments (cf. 104 or 105), to monomeric plasticizers (cf. 102) among others. Entries 88–90, 102 were transparent while entries 91–99, 103 were transparent but, as expected, hazy due to the inorganics or organics added to the blend. Entries 99 and 100 were white because of the TiO$_2$ while 104 and 105 were blue because of the TiO$_2$ and dye; these examples show that the blends can be readily pigmented or dyed. As can be seen from Table X, these additives have little or no effect on the mechanical properties or tear strength of films prepared from the blends (cf. Tables X and VI). Hence, additives e.g., CaCO$_3$ or microcrystalline cellulose which promote biodegradation can be added to the blends while maintaining a wide range of physical properties for materials prepared from the blends by proper selection of the blend composition.

Example 6

Ternary blends of cellulose acetate propionate with a DS/AGU of 2.74, aliphatic polyesters, and a third polymer component were prepared using the standard procedures. Table XI gives the mechanical properties, tear strength, and clarity of the films made from the blends.

TABLE XI

Mechanical Properties, Tear Strength, and Clarity of Films Prepared From CAP (DS/AGU = 2.75)/Aliphatic Polyester or Aliphatic-Aromatic Copolyester/Polymer Ternary Blends

| Entry | Polyester/Polymer | Elongation at Break (%) | Tangent Modulus ($10^5$ psi) | Tensile Strength ($10^3$ psi) | Tear Strength (g/mil) | Clarity |
|---|---|---|---|---|---|---|
| 106 | 40% PTG<br>2% Polyvinyl Alcohol<br>(100% hydrolyzed, MW = 115,000)<br>0.5% Myvaplex 600 | 29 | 0.09 | 0.70 | 13.6 | − |
| 107 | 40% PTG<br>5% Polyvinyl Alcohol<br>(100% hydrolyzed, MW = 115,000)<br>0.5% Myvaplex 600 | 31 | 0.05 | 0.60 | 14.4 | − |
| 108 | 40% PTG<br>5% Polyvinyl Alcohol<br>(98-99% Hydrolyzed,<br>MW = 31,000–50,000)<br>0.5% Myvaplex 600 | 68 | 0.05 | 1.28 | 11.3 | − |
| 109 | 40% PTG<br>2% Polyvinyl Alcohol<br>(87–89% hydrolyzed,<br>MW = 124–186 K)<br>0.5% Myvaplex 600 | 35 | 0.14 | 0.67 | 12.2 | − |
| 110 | 40% PTG<br>5% Polyvinyl Alcohol<br>(87–89% hydrolyzed,<br>MW = 124–186 K)<br>0.5% Myvaplex 600 | 37 | 0.10 | 0.70 | 14.4 | − |
| 111 | 40% PTG<br>5% Polyvinyl Alcohol<br>(87–89% hydrolyzed,<br>M = 31,000–50,000)<br>0.5% Myvaplex 600 | 67 | 0.11 | 1.32 | 11.9 | − |
| 112 | 40% PTG<br>5% Polyvinyl Alcohol<br>(80% Hydrolyzed<br>MW = 9,000–10,000) | 93 | 0.08 | 1.93 | 10.1 | + |
| 113 | 38% PTG<br>2% ECDEL 9810 | 49 | 0.06 | 0.65 | 12.7 | ± |
| 114 | 35% PTG<br>5% Nylon 6 | 74 | 0.32 | 2.11 | 15.0 | − |
| 115 | 37.5% PTG<br>2.5% Nylon | 92 | 0.09 | 1.09 | 13.7 | ± |
| 116 | 40% PTG<br>2% PVA, 0.5% MYVAPLEX 600 | 72 | 0.17 | 1.38 | 15.0 | + |
| 117 | 40% PTG<br>5% PVA, 0.5% MYVAPLEX 600 | 93 | 0.11 | 1.56 | 18.3 | + |
| 118 | 40% PTG<br>10% PVA | 88 | 0.10 | 1.55 | 14.4 | ± |
| 119 | 28% PEG<br>52% PVA | 306 | 0.05 | 1.28 | NT | ± |
| 120 | 31% PEG<br>59% PVA | 509 | 0.02 | 1.06 | NT | ± |
| 121 | 40% PTG<br>5% PMMA, 0.5% MYVAPLEX 600 | 86 | 0.12 | 1.45 | 17.4 | + |
| 122 | 40% PTG<br>2% PMMA, 0.5% MYVAPLEX 600 | 61 | 0.17 | 1.15 | 12.4 | + |
| 123 | 40% PTG<br>10% PMMA | 75 | 0.10 | 1.48 | 11.3 | + |
| 124 | 40% PTG<br>5% PEMA, 0.5% MYVAPLEX 600 | 48 | 0.17 | 0.93 | 16.2 | + |
| 125 | 40% PTG<br>2% PEMA, 0.5% MYVAPLEX 600 | 71 | 0.19 | 1.23 | 13.2 | + |
| 126 | 40% PTG<br>10% PEMA | 57 | 0.10 | 0.94 | 13.9 | + |
| 127 | 35% PTG<br>5% Hydroxypropyl Cellulose<br>(MW = 100,000) | 70 | 0.20 | 1.80 | 20.3 | + |
| 128 | 39% PTG<br>1% Hydroxypropyl Cellulose<br>(MW = 1,000,000) | 80 | 0.15 | 1.71 | 21.2 | + |
| 129 | 35% PTG<br>5% Hydroxypropyl Celluloae<br>(MW = 1,000,000) | 80 | 0.22 | 1.74 | 16.9 | + |
| 130 | 40% PTG<br>2% Ethylene/Vinyl Acetate | 81 | 0.02 | 0.60 | 11.1 | + |

TABLE XI-continued

Mechanical Properties, Tear Strength, and Clarity of Films Prepared
From CAP (DS/AGU = 2.75)/Aliphatic Polyester or Aliphatic-Aromatic
Copolyester/Polymer Ternary Blends

| Entry | Polyester/Polymer | Elongation at Break (%) | Tangent Modulus ($10^5$ psi) | Tensile Strength ($10^3$ psi) | Tear Strength (g/mil) | Clarity |
|---|---|---|---|---|---|---|
| | Copolymer (40% vinyl acetate) | | | | | |
| 131 | 35% PTG | 59 | 0.29 | 1.92 | 11.5 | + |
| | 2% Ethylene/Vinyl Acetate Copolymer (40% vinyl acetate) | | | | | |
| 132 | 35% PTG | 43 | 0.20 | 1.40 | 10.9 | + |
| | 5% Ethylene/Vinyl Acetate Copolymer (40% vinyl acetate) | | | | | |
| 133 | 35% PTG | 44 | 0.08 | 0.98 | 8.8 | ± |
| | 10% Ethylene/Vinyl Acetate Copolymer (40% vinyl acetate) | | | | | |
| 134 | 35% PTG | 35 | 0.46 | 1.09 | 8.0 | + |
| | 2% Ethylene/Vinyl Acetate Copolymer (50% vinyl acetate) | | | | | |
| 135 | 35% PTG | 35 | 0.13 | 1.03 | 8.7 | + |
| | 5% Ethylene/Vinyl Acetate Copolymer (50% vinyl acetate) | | | | | |
| 136 | 35% PTG | 28 | 0.05 | 0.80 | 10.4 | ± |
| | 10% Ethylene/Vinyl Acetate Copolymer (SO% vinyl acetate) | | | | | |
| 137 | 35% PTG | 68 | 0.28 | 1.93 | 13.3 | + |
| | 2% Ethylene/Vinyl Acetate Copolymer (70% vinyl acetate) | | | | | |
| 138 | 35% PTG | 67 | 0.24 | 1.86 | 14.5 | + |
| | 5% Ethylene/Vinyl Acetate Copolyer (70% vinyl acetate) | | | | | |
| 139 | 35% PTG | 79 | 0.17 | 1.67 | 12.5 | ± |
| | 10% Ethylene/Vinyl Acetate Copolyrner (70% vinyl acetate) | | | | | |
| 140 | 40% PTG | 75 | 0.07 | 1.40 | nm | – |
| | 2% Lexan Polycarbonate | | | | | |
| 141 | 40% PTG | 70 | 0.08 | 1.28 | nm | – |
| | 5% Lexan Polycarbonate | | | | | |
| 142 | 40% PTG | 65 | 0.04 | 1.15 | nm | – |
| | 10% Lexan Polycarbonate | | | | | |

As Table XI shows, cellulose esters and aliphatic polyesters or aliphatic-aromatic copolyesters can be blended with other polymers to form either miscible or partially miscible ternary blends which have excellent physical properties. Entries 112, 116, 117, 119–130, 132, 133, 135, and 136 are examples of miscible ternary blends while the remaining examples are ternary blends which are partially miscible. These blends can, of course, contain immiscible additives demonstrated in Example 5 or in Example 7 (vide infra).

Example 7

Ternary blends of cellulose esters and aliphatic polyesters or aliphatic-aromatic copolyester, and a hydrophobic additive were prepared using the standard procedures. Tables XII and XIII gives the DS/AGU, IV, and clarity of the blends as well as the mechanical properties, tear strength, and water vapor transmission rates of the films made from the blends.

TABLE XII

DS/AGU, IV, and Clarity of Cellulose Ester/Polyester Blends
Containing Hydrophobic Additives

| Entry | Polyester/Hydrophobic Additive | $DS_{Ac}$ | $DS_{Pr}$ | $DS_{Bu}$ | IV CE | IV PE | IV Blend | Clarity |
|---|---|---|---|---|---|---|---|---|
| 143 | 39.95% PTG | 0.10 | 2.64 | — | 1.3 | 1.1 | nm | + |
| | 0.05% MYVAPLEX 600 | | | | | | | |
| 144 | 39.9% PTG | 0.10 | 2.64 | — | 1.3 | 1.1 | nm | + |
| | 0.1% MYVAPLEX 600 | | | | | | | |
| 145 | 39.75% PTG | 0.10 | 2.64 | — | 1.3 | 1.1 | nm | + |
| | 0.25% MYVAPLEX 600 | | | | | | | |
| 146 | 39.5% PTG | 0.10 | 2.64 | — | 1.3 | 1.1 | nm | + |
| | 0.5% MYVAPLEX 600 | | | | | | | |
| 147 | 39.25% PTG | 0.10 | 2.64 | — | 1.3 | 1.1 | nm | + |
| | 0.75% MYVAPLEX 600 | | | | | | | |
| 148 | 39% PTG | 0.10 | 2.64 | — | 1.3 | 1.1 | 1.19 | + |
| | 1% MYVAPLEX 600 | | | | | | | |

TABLE XII-continued

DS/AGU, IV, and Clarity of Cellulose Ester/Polyester Blends Containing Hydrophobic Additives

| Entry | Polyester/Hydrophobic Additive | $DS_{Ac}$ | $DS_{Pr}$ | $DS_{Bu}$ | IV CE | IV PE | IV Blend | Clarity |
|---|---|---|---|---|---|---|---|---|
| 149 | 38.5% PTG 1.5% MYVAPLEX 600 | 0.10 | 2.64 | — | 1.3 | 1.1 | 1.22 | + |
| 150 | 38% PTG 2% MYVAPLEX 600 | 0.10 | 2.64 | — | 1.3 | 1.1 | 1.18 | + |
| 151 | 39% PTG 1% MYVACET 507 | 0.10 | 2.64 | — | 1.3 | 1.1 | 1.23 | + |
| 152 | 39% PTG 1% MYVACET 707 | 0.10 | 2.64 | — | 1.3 | 1.1 | 1.22 | + |
| 153 | 39% PTG 1% MYVACET 908 | 0.10 | 2.64 | — | 1.3 | 1.1 | 1.23 | + |
| 154 | 39% PTG 1% MYVEROL 18-07 | 0.10 | 2.64 | — | 1.3 | 1.1 | nm | + |
| 155 | 39% PTG 1% MYVEROL 18-35 | 0.10 | 2.64 | — | 1.3 | 1.1 | nm | + |
| 156 | 39% PTG 1% MYVEROL 18-99 | 0.10 | 2.64 | — | 1.3 | 1.1 | nm | + |
| 157 | 39% PTG 1% paraffin | 0.10 | 2.64 | — | 1.3 | 1.1 | 1.21 | + |
| 158 | 38% PTG 2% paraffin | 0.10 | 2.64 | — | 1.3 | 1.1 | 1.18 | + |
| 159 | 49% PEG(T) (70/30) 1% MYVAPLEX 600 | 0.10 | 2.64 | — | 1.3 | 0.6 | 0.89 | + |

TABLE XIII

Mechanical Properties, Tear Strength, Water Vapor Transmission Rates of Films Prepared from Cellulose Ester/Polyester Blends Containing Hydrophobic Additives

| Entry | Polyester/Hydrophobic Additive | Elongation at Break (%) | Tangent Modulus ($10^5$) | Tensile Strength ($10^3$) | Tear Strength (g/mil) | WVTR (g mil/100 in$^2$-24 hours) |
|---|---|---|---|---|---|---|
| 143 | 39.95% PTG 0.05% MYVAPLEX 600 | 75 | 0.13 | 1.66 | 9.6 | 306 |
| 144 | 39.9% PTG 0.1% MYVAPLEX 600 | 92 | 0.17 | 2.06 | 11.6 | <500 |
| 145 | 39.75% PTG 0.25% MYVAPLEX 600 | 78 | 0.16 | 1.64 | 9.5 | 244 |
| 146 | 39.5% PTG 0.5% MYVAPLEX 600 | 93 | 0.11 | 2.10 | 14.9 | 227 |
| 147 | 39.25% PTG 0.75% MYVAPLEX 600 | 81 | 0.11 | 1.67 | 12.8 | 171 |
| 148 | 39% PTG 1% MYVAPLEX 600 | 71 | 0.11 | 1.47 | 10.8 | 103 |
| 149 | 38.5% PTG 1.5% MYVAPLEX 600 | 75 | 0.12 | 1.71 | 14.0 | 159 |
| 150 | 38% PTG 2% MYVAPLEX 600 | 62 | 0.11 | 1.45 | 9.8 | 178 |
| 151 | 39% PTG 1% MYVACET 507 | 82 | 0.11 | 1.76 | 12.7 | 200 |
| 152 | 39% PTG 1% MYVACET 707 | 64 | 0.09 | 1.69 | 9.5 | 261 |
| 153 | 39% PTG 1% MYVACET 908 | 75 | 0.09 | 2.39 | 12.6 | 258 |
| 154 | 39% PTG 1% MYVEROL 18-07 | 62 | 0.15 | 1.27 | 12.5 | 146 |
| 155 | 39% PTG 1% MYVEROL 18-35 | 92 | 0.07 | 2.04 | 12.2 | 181 |
| 156 | 39% PTG 1% MYVEROL 18-99 | 75 | 0.08 | 1.32 | 13.7 | 397 |
| 157 | 39% PTG 1% paraffin | 105 | 0.10 | 2.35 | 15.9 | 238 |
| 158 | 38% PTG 2% paraffin | 65 | 0.15 | 1.66 | 17.1 | 231 |
| 159 | 49% PEG(T)[70/30] 1% MYVAPLEX 600 | 48 | 0.10 | 1.35 | 7.6 | 106 |

The examples of Tables XII and XIII illustrate that hydrophobic additives can be added to blends of cellulose esters and aliphatic polyesters or aliphatic-aromatic copolyesters to control water vapor transmission rates of materials prepared from the blends without loss of mechanical properties or tear strength. For example, the WVTR of the films prepared from a CAP/PTG blend containing 0.25–1% MYVAPLEX 600 was controlled between 244 to 103 g mil/100 in$^2$-24 hours (cf entries 143–146). With increasing hydrophobic additive, the WVTR decreased until the WVTR leveled off at around 1% additive.

Example 8

Preparation of a 65/35 blend of CAP(DS$_{Ac}$=0.10, DS$_{Pr}$=2.64)/poly(tetramethylene glutarate) on the 30 mm W-P twin screw extruder was performed under the following conditions according to the general procedure.

Feed rate for poly(tetramethylene glutarate)=15.0 lb/hr

Feed rate for CAP=28.0 lb/hr

Total output from extruder=43 lb/hr

Feed Line temperature=190° C.

RPM of the Screw=207

Torque=30%

Extruder zone temperatures: Zone 1=180° C.; Zones 2–7=230° C.

Example 9

Other blends, including 10, 20, and 40 wt. % polytetramethylene glutarate with CAP (DS$_{Ac}$=0.10, DS$_{Pr}$=2.64) were also prepared on the W-P extruder according to the general procedure except that the polyester was added by mixing solid poly(tetramethylene glutarate) with CAP(DS$_{Ac}$=0.10, DS$_{Pr}$=2.64) and feeding both materials into Zone 1 of the extruder under otherwise similar conditions.

Example 10

Blends prepared as in Examples 8 and 9 were molded on a Toyo 90 injection molding machine under the following conditions. These conditions should not be considered the ideal conditions, but are typical of those that can be used on blends of this type.

Nozzle temperature=200° C.

Zone 1 temperature=210° C.

Zone 2 temperature=210° C.

Zone 3 temperature=190° C.

Zone 4 temperature=180° C.

Melt temperature=215° C.

Injection and Hold Pressures=750 psig

Mold temperature=14° C.

Screw speed=75 rpm

Example 11

The physical properties of the blends prepared as in Example 10 are shown in Table XIV as well as physical properties of the CAP containing 12% monomeric plasticizer.

TABLE XIV

Physical Properties of Blends of CAP (DS$_{Ac}$ = 0.10, DS$_{Pr}$ = 2.64) and Poly(Tetramethylene Glutarate)

| Property (units) | 10% PTG | 20% PTG | 35% PTG | 40% PTG | 12% DOA |
|---|---|---|---|---|---|
| Tensile Strength (10$^3$ psi) | 7.9 | 5.3 | 2.8 | 2.3 | 4.76 |
| Elongation at break (%) | 14 | 41 | 72 | 93 | 27 |
| Flexural Modulus (10$^5$ psi) | 3.3 | 2.1 | 0.78 | 0.18 | 2.16 |
| Izod Impact 23° C. (ft-lb/in) | 1.7 (C) | 4.6 (C) | 15.4 (PB) | 12.9 (NB) | 7.43 |
| HDT (° C.) | 81 | 54 | 41 | NT | 67 |

This example demonstrates that aliphatic polyesters blend components are very effective non-volatile, non-extractable polymeric additives. These blends offer many superior physical properties relative to a CAP containing a monomeric plasticizer. For example, relative to the a CAP containing 12% DOA, the blend containing 10% PTG has superior tensile strength, flexural modulus, and a higher heat deflection temperature.

Example 12

The physical properties blends prepared as in Example 10 are shown in Table XIV.

TABLE XV

Physical Properties of Blends of CAP (DS$_{Ac}$ = 0.10, DS$_{Pr}$ = 2.64) and Aliphatic-Aromatic Polyesters as well as Physical Properties of the CAP Containing 12% Monomeric Plasticizer

| Property (units) | 8% PEG(T) [70/30] | 16% PEG(T) [70/30] | 24% PEG(T) [70/30] | 8% PTG(T) [60/40] | 16% PTG(T) [60/40] | 24% PTG(T) [60/40] | 12% DOA |
|---|---|---|---|---|---|---|---|
| Tensile Strength (10$^3$ psi) | 8.32 | 8.79 | 7.46 | 8.67 | 8.64 | 7.79 | 4.76 |
| Elongation at break (%) | 8 | 8 | 14 | 11 | 11 | 17 | 27 |
| Flexural Modulus (10$^5$ psi) | 3.53 | 3.23 | 2.52 | 3.43 | 3.25 | 2.72 | 2.16 |
| Flexural Strength (10$^3$ psi) | 10.43 | 9.98 | 7.97 | 10.82 | 10.32 | 8.74 | 5.67 |
| Izod Impact 23° C. | 1.63 | 1.70 | 1.82 | 3.00 | 2.69 | 2.96 | 7.43 |

TABLE XV-continued

Physical Properties of Blends of CAP ($DS_{Ac}$ = 0.10, $DS_{Pr}$ = 2.64) and Aliphatic-Aromatic Polyesters as well as Physical Properties of the CAP Containing 12% Monomeric Plasticizer

| Property (units) | 8% PEG(T) [70/30] | 16% PEG(T) [70/30] | 24% PEG(T) [70/30] | 8% PTG(T) [60/40] | 16% PTG(T) [60/40] | 24% PTG(T) [60/40] | 12% DOA |
|---|---|---|---|---|---|---|---|
| (ft-lb/in) Izod Impact −40° C. (ft-lb/in) | 0.77 | 0.76 | 0.25 | 2.16 | 2.11 | 2.23 | 2.94 |
| HDT 66 psi (° C.) | 82 | 66 | 52 | 93 | 74 | 59 | 67 |

This example demonstrates that aliphatic-aromatic polyesters blend components are very effective non-volatile, non-extractable polymeric additives. These blends offer many superior physical properties relative to a CAP containing a monomeric plasticizer. For example, relative to the a CAP containing 12% DOA, all of the above blends at similar polymer content have superior tensile strengths, flexural moduli, and flexural strengths as well as higher heat deflection temperatures. This example also teaches some of the physical property differences between a miscible, i.e., PEG(T) [70/30], cellulose ester/aliphatic-aromatic blend and a partially miscible, i.e., PEG(T) [60/40], cellulose ester/aliphatic-aromatic blend. In general, the partially miscible blend offers superior Izod impact strengths, particularly at −40° C.

Example 13

TABLE XVI

Inherent Viscosity, Water Vapor Transmission Rates, Mechanical Properties, and Tear Strength of Films Prepared From Aliphatic-Aromatic Copolyesters

| Entry | Polyester | Elongation at Break (%) | Tangent Modulus ($10^5$ psi) | Tensile Strength ($10^3$ psi) | Tear Strength (g/mil) | IV | WVTR (g/100 in$^2$-24 hours) |
|---|---|---|---|---|---|---|---|
| 160 | PHG(T) [50/50] | 357 | 0.09 | 0.73 | 26 | 0.72 | 65 |
| 161 | PTG(T) [60/40] | 908 | 0.05 | 1.95 | 214 | 1.15 | 137 |
| 162 | PTG(T) [40/60] | 642 | 0.23 | 3.07 | 115 | 0.94 | 52 |
| 163 | PTS(T) [70/30] | 722 | 0.41 | 4.48 | 59 | nm | nm |
| 164 | PTS(T) [85/15] | 732 | 0.28 | 3.99 | 42 | 1.03 | 42 |
| 165 | PTG(T) [55/45] | 738 | 0.08 | 3.54 | 142 | 1.11 | nm |
| 166 | PTG(T)(D) [50/45/5] | 927 | 0.05 | 5.22 | 126 | 1.23 | nm |

These examples illustrate that films prepared from aliphatic-aromatic copolyesters have very high elongation, high tear strengths, low WVTR, and low moduli and hence are useful in film applications.

Example 14

The physical properties of AAPE molded bars

TABLE XVII

Physical Properties of AAPE

| Property (units) | PTS(T) [85/15] | PTS(T) [70/30] | PTG(T) [50/50] |
|---|---|---|---|
| Tensile Strength ($10^3$ psi) | 2.89 | 1.79 | 1.51 |
| Elongation at break (%) | 482 | 384 | 437 |
| Flexural Modulus ($10^5$ psi) | 0.57 | 0.20 | 0.13 |
| Izod Impact 23° C. (ft-lb/in) | 6.0 (NB) | 6.5 (NB) | 3.2 (NB) |
| Izod Impact −40° C. (ft-lb/in) | 0.44 (CB) | 0.86 (CB) | 8.23 (NB) |

This example demonstrates that AAPEs have very high elongation at break, low flexural modulus and excellent Izod Impacts.

Example 15

A variety of conditions are available for producing melt blown films from the blends of this invention. Temperature set points for the extruders can vary depending on the level of additives, if any. For this example, all heater zones were set between 190 and 200° C. with a screw rpm of 25 to 30. This produced a measured melt temperature of 183° C. Heater temperatures must be increased, especially in the die area, by 5 to 10° C. if higher levels of $TiO_2$ (or any antiblocks such as talc or diatomaceous earth) are used in order to prevent clogging of the die. Temperature settings will also vary depending on the type of screw used and the size of the extruder. The preferred temperatures are 175–215° C. Blowing conditions can be characterized by the blow up ratio (BUR), the ratio of bubble diameter to die diameter which gives an indication of hoop or transverse direction (TD) stretch; or the draw-down ratio (DDR), which is an indication of the axial or machine direction (MD) stretch. If the BUR and DDR are equal then the amount of stretch in the MD and TD is approximately the same resulting in "balanced" film.

Blown film was produced from a blend consisting of 98% of a 60/40 blend of cellulose acetate propionate ($DS_{Ac}$=0.10, $DS_{Pr}$=2.64) and poly(tetramethylene glutarate), and 2% $TiO_2$. The $TiO_2$, added in the form of a masterbatch (blended at a level of 20% and pelletized), was added in order to obtain an opaque film. The blown film was produced using a laboratory scale blown film line which consisted of a Killion 1.25 inch extruder with a 15:1 gear reducer. The screw was a Maddock mixing type with an L/D of 24 to 1 although a general purpose screw has also been used. Compression ratio for the mixing screw was 3.5:1. A 1.21 inch die with a 5 mil die gap was used. The air ring was a Killion single-lip, No. 2 type. Prior to processing, the blends were dried overnight at 50° C. in dehumidified air dryers.

For this example, the BUR was 2.20 and the DDR was 1.13 resulting in a film with an average thickness of 2 mils. This produced a film with average tear strengths of 8.9 and 7.5 g/mil in the MD and TD, respectively. Additionally, elongation to break values for these directions are 101 and 79%, tangent moduli are 30 and 24 ksi, and break stresses are 3.9 and 3.6 ksi. BUR values have been tried ranging from 2 to 3.9 and DDR values from 0.5 to 20 by changing blow conditions and also going to a thicker die gap. Increasing these parameters generally results in improved properties except for % elongation which is reduced. For example, a 0.5 mil film with a BUR of 2.76 and a DDR of 3.89 had average tear strengths of 31.3 and 29.7 g/mil, elongation to break values of 74 and 37%, moduli of 57 and 86 ksi, and break stresses of 3.2 and 4.9 ksi for the MD and TD, respectively.

Example 16

Blown film was produced from blends consisting of cellulose acetate propionate ($DS_{Ac}$=0.10, $DS_{Pr}$=2.64) and poly(tetramethylene glutarate-co-terephthalate). The blown film was produced using a laboratory scale blown film line which consisted of a Killion 1.25 inch extruder with a 15:1 gear reducer. The screw was a Maddock mixing type with an L/D of 24 to 1 although a general purpose screw has also been used. Compression ratio for the mixing screw was 3.5:1. A 1.21 inch die with a 25 mil die gap was used. The air ring was a Killion single-lip, No. 2 type. Prior to processing, the blends were dried overnight at 50° C. in dehumidified air dryers. The results are given in Table XVII.

TABLE XVIII

Conditions and Results for Blown Film of a Cellulose Acetate Propionate and Poly (tetramethylene Glutarate-co-terephthalate)

| Entry[a] | Description[b] | Film Thickness (mils) | BUR | DDR | Tear[c] Strength (g/mil) | Elongation[c] (%) | Tangent[c] Modulus (ksi) |
|---|---|---|---|---|---|---|---|
| 167 | 35/65 [50/50] | 2.41 | 3.2 | 3.9 | 50.8 13.4 | 80 156 | 55 37 |
| 168 | 25/75 [50/50] | 1.21 | 3.1 | 8.1 | 57.7 49.0 | 121 257 | 24 19 |
| 169 | 35/65 [55/45] | 2.11 | 2.6 | 4.6 | 74.8 15.5 | 123 161 | 36 33 |
| 170 | 25/75 [55/45] | 1.95 | 2.6 | 4.9 | 101.1 59.7 | 121 344 | 35 23 |
| 171 | 35/65 [60/40] | 2.19 | 2.6 | 4.4 | 36.6 29.4 | 124 178 | 18 9 |

[a]Each sample contained inorganics.
[b]The first ratio (e.g., 35/65) is the ratio of cellulose ester to copolyester in the blend. The second ratio (e.g., [50/50]) is the ratio of glutarate to terephthalate in the copolyester.
[c]The first value is for the machine direction and the second value is for the transverse direction.

The entries of this example demonstrate that film blown from blends of cellulose acetate propionate and aliphatic-aromatic copolyesters have very high tear strengths and elongation at break. Moreover, physical properties such as tear strength can be high in one direction or can be roughly equal in both directions demonstrating that this film can be oriented. In general, a balanced film is obtained by choice of the DDR/BUR ratio.

Example 17

An 80/20 blend of cellulose acetate propionate ($DS_{Ac}$=0.10, $DS_{Pr}$=2.64)/poly(tetramethylene glutarate) was used to spin fibers using a 54 hole round and Y jet (55 micron equivalent diameter) at an extrusion temperature of 215° C. and a takeup of 250 m/m or 600 m/m. Packages were doffed and plied together onto cones making 270 filament yarn. A two step draw process was used to make drawn fiber. Table XV gives representative data for both drawn and undrawn fiber. Photomicrographs showed that the fibers had excellent cross-sectional stability.

TABLE XIX

Strand Tensiles of Fiber Melt-Spun From an 80/20 Blend of Cellulose Acetate
Propionate/Poly (Tetramethylene Glutarate)

| Entry | Temp (°C.)/Draw Ratio | Denier | Tenacity | Elongation | Modulus g/Denier | Toughness g/Denier |
|---|---|---|---|---|---|---|
| 172 | undrawn | 905 | 0.42 | 38 | 16 | 0.14 |
| 172B | 70/1.82 | 486 | 0.98 | 4 | 45 | 0.02 |
| 173 | undrawn | 1478 | 0.54 | 49 | 16 | 0.21 |
| 173B | 85/1.75 | 892 | 0.93 | 5 | 41 | 0.03 |
| 174 | undrawn | 877 | 0.66 | 26 | 19 | 0.14 |
| 174B | 70/1.33 | 673 | 1.02 | 4 | 42 | 0.03 |
| 175 | undrawn | 898 | 0.55 | 26 | 17 | 0.12 |
| 175B | 70/1.40 | 655 | 0.88 | 3 | 42 | 0.01 |

Biodegradation Studies

Figure 1B:
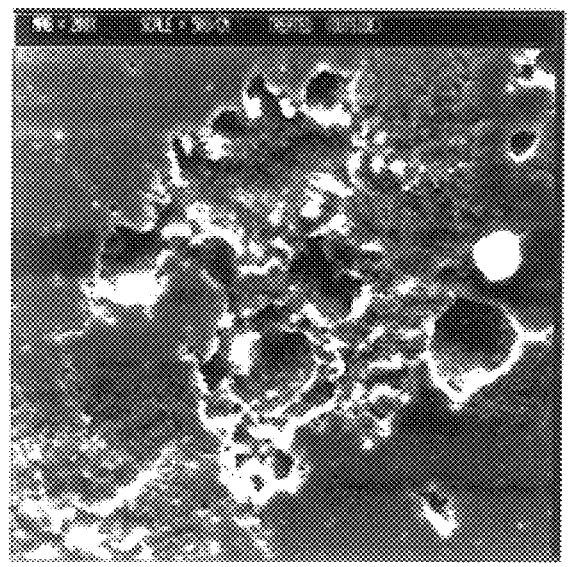
FIG. 1B—SEM photograph of the outer, smooth surface of a cellulose acetate (DS=1.7) film formed by drawing a film from a 20 wt. % solution of cellulose acetate in a 50/50 (vol./vol.) mixture of water/acetone after four days incubation in an in vitro microbial enrichment system. Magnification is 200×.
Figure 2A:
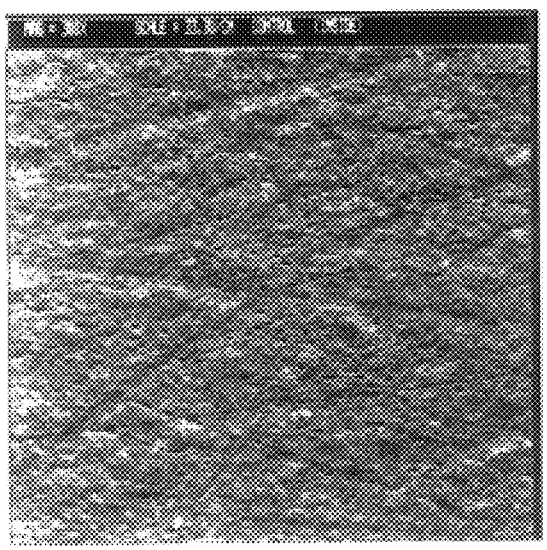
FIG. 2A—SEM photograph of the inner, rough surface of a cellulose acetate (DS=1.7) film formed by drawing a film from a 20 wt. % solution of cellulose acetate in a 50/50 (vol./vol.) mixture of water acetone. Magnification is 300×.
Figure 2B:
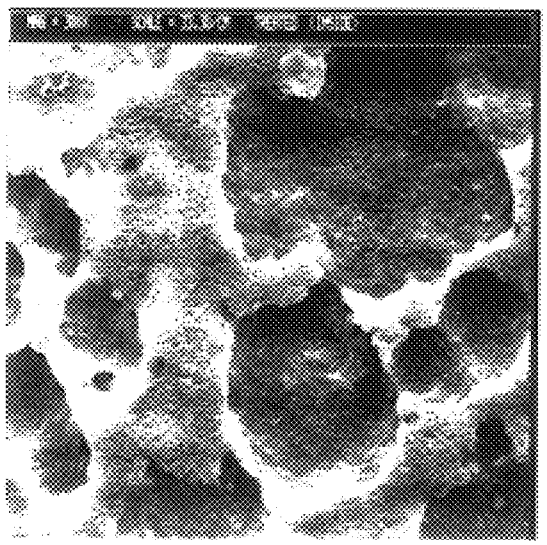
FIG. 2B—SEM photograph of the inner, rough surface of a cellulose acetate (DS=1.7) film formed by drawing a film from a 20 wt. % solution of cellulose acetate in a 50/50 (vol./vol.) mixture of water acetone after four days incubation in an in vitro microbial enrichment system. Magnification is 300×.
Figure 3:
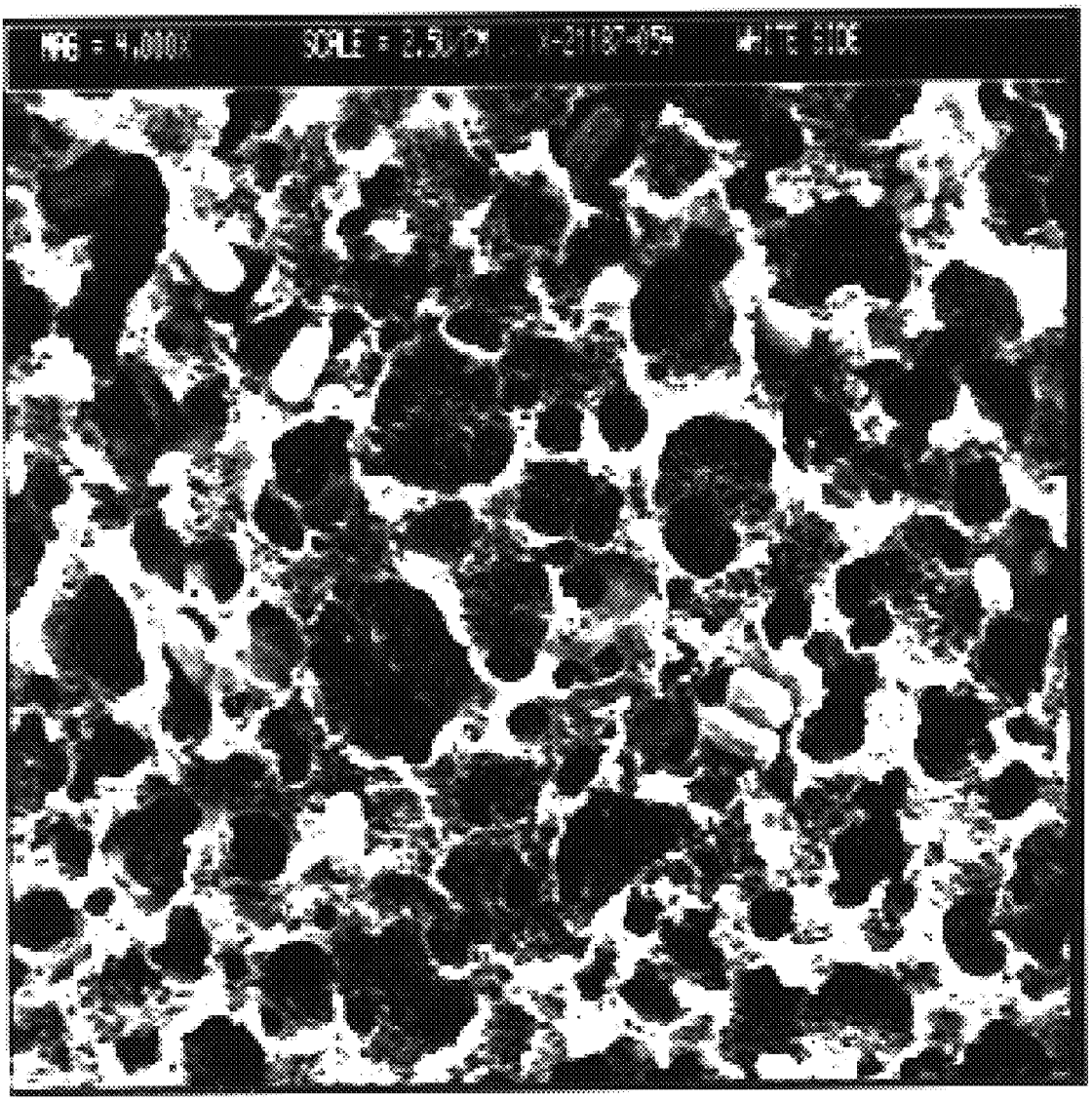
FIG. 3—SEM photograph of the outer, smooth surface of a cellulose acetate (DS=1.7) film formed by drawing a film from a 20 wt. % solution of cellulose acetate in a 50/50 (vol./Vol.) mixture of water/acetone after four days incubation in an in vitro microbial enrichment system from which the bacteria has not been washed. Magnification is 4,000×.
Figure 4:
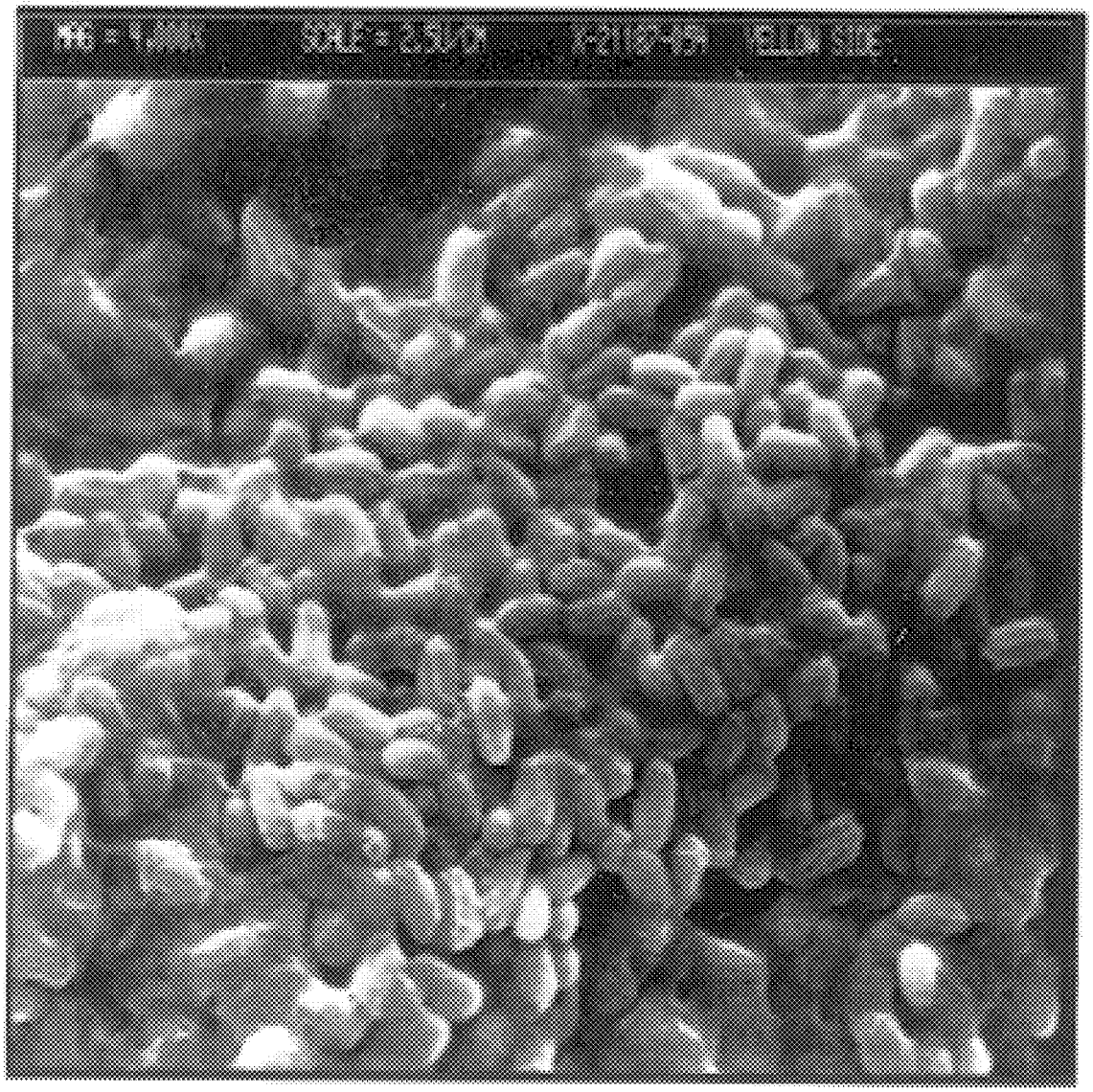
FIG. 4—SEM photograph of the inner, rough surface of a cellulose acetate (DS=1.7) film formed by drawing a film from a 20 wt. % solution of cellulose acetate in a 50/50 (vol./vol.) mixture of water/acetone after four days incubation in an in vitro microbial enrichment system from which the bacteria have not been washed. Magnification is 4,000×.

Although it is evident that polyhydroxyalkanoates are biodegradable under the appropriate conditions, it is not known in the art that cellulose esters are biodegradable since it is widely believed that the acyl substituents shield the cellulose backbone from microbial attack. We have found that when films of cellulose acetate having a degree of substitution of 1.7 were immersed in the Tennessee Eastman (Kingsport, Tenn., U.S.A.) wastewater treatment facility, extensive degradation of the films occurred within 27 days. In addition, a culture consisting of a mixed population of microbes isolated from the activated sludge obtained from the same wastewater treatment facility were grown in the presence of films of the same cellulose acetate (DS=1.7). In this case, extensive degradation of the cellulose acetate films was observed after 5 days. FIGS. 1A, 1B, 2A, and 2B show scanning electron microscopy (SEM) photographs of the two sides of cellulose acetate films formed by drawing a film from a solution consisting of 20% cellulose acetate (DS=1.7) by weight in a 50/50 mixture of water/acetate. FIGS. 1A and 2A are of a control film while FIGS. 1B and 2B are of a film on which the culture, consisting of a mixed population of microbes isolated from the activated sludge, were grown for 4 days. In FIGS. 1B and 2B, extensive degradation of the cellulose acetate film is evident. Comparison of the control films in FIGS. 1A and 2A shows that the film sides are different. FIG. 1A shows the outer, smooth surface of the film which results from shearing by the draw blade while FIG. 2A shows the inner, rough surface of the film which was in contact with the surface on which the film was cast. Comparison of FIGS. 1B and 2B shows that the rough or inner side of the film was more extensively degraded. A rough surface area promotes attachment of the bacteria leading to a more rapid rate of degradation. Processes, such as foamed films and the like, which promote rough surfaces are desirable in the practice of this invention. FIGS. 3 and 4 show SEM photographs of the smooth and rough sides of a cellulose acetate film from which the bacteria were not washed. In addition to showing extensive pitting of the film surface due to degradation of the cellulose acetate, these films show the attached microbes in the cavities where degradation is occurring.

In vitro Enrichment System: fresh composite samples of activated sludge are obtained from the AA 03 aeration basins in the Tennessee Eastman (Kingsport, Tenn., U.S.A.) wastewater treatment plant which has a design capacity of receiving 25 million gallons of waste per day with BOD concentration up to 200,000 pounds per day. The major waste components consist largely of methanol, ethanol, isopropanol, acetone, acetic acid, butyric acid, and propionic acid. The sludge operating temperatures vary between 35° C. to 40° C. In addition, a dissolved oxygen concentration of 2.0 to 3.0 and a pH of 7.1 are maintained to insure maximal degradation rates. The activated sludge serves as the starting inoculum for the stable mixed population of microbes used in this invention. A stable population is obtained by serially transferring the initial inoculum (5% v/v) to a basal salt media containing glucose or cellobiose, acetate, and cellulose acetate (DS=2.5).

Cellulose ester film degrading enrichments are initiated in a basal salts medium containing the following ingredients per liter: 50 mL of Pfennig's Macro-mineral solution, 1.0 mL of Pfennig's trace element solution, 0.1% (wt/vol) Difco yeast extract, 2 mM $Na_2SO_4$, 10 mM $NH_4C_1$ which supplements the ammonia levels provided by Pfennig's Macro-mineral solution, 0.05% (wt/vol) cellobiose, 0.05% (wt/vol) NaOAc. This solution is adjusted to pH 7.0 and a final volume of 945 mL before being autoclaved at 121° C. at 15 psi for 15 minutes. After cooling to room temperature, 50 mL of sterile 1 M phosphate buffer and 5 mL of a complex vitamin solution which has been filtered through a 0.02 mm filter are added. The test cellulosic film is then added and the flask is inoculated (5% v/v) with a stable mixed population enrichment. The flask is placed in a New Brunswick incubator and held at 30° C. and 250 rpm for the appropriate period. Initially, the films are often observed to turn cloudy and to be coated with a yellow affinity substance (Current Microbiology, 9, 195 (1983)), which is an indication of microbial activity. After 4 to 12 days, the films are broken into small pieces at which time they are harvested by pouring the media through a filter funnel. The pieces are collected and washed with water. The film pieces are suspended in a neutral detergent solution at 90° C. for 30–60 minutes before washing extensively with water. The films are placed in a vacuum oven at 40° C. until dry before weighing. In each experiment, control experiments are conducted in which the films are subjected to the same experimental protocol except inoculation with the microbes.

Cellulose Acetate, DS=1.7.

| Film Number | Original Weight (mg) | Final Weight (mg) | % Weight Loss |
|---|---|---|---|
| 1* | 190 | 181 | 5 |
| 2* | 233 | 220 | 6 |
| 3* | 206 | 196 | 5 |
| 4 | 134 | 2 | 99 |
| 5 | 214 | 35 | 84 |
| 6 | 206 | 16 | 92 |
| 7 | 195 | 184 | 5 |
| 8 | 187 | 175 | 6 |
| 9 | 177 | 3 | 98 |

-continued

| Film Number | Original Weight (mg) | Final Weight (mg) | % Weight Loss |
|---|---|---|---|
| 10 | 181 | 5 | 97 |
| 11* | 167 | 164 | 2 |
| 12* | 174 | 173 | 1 |

-continued

| Film Number | Original Weight (mg) | Final Weight (mg) | % Weight Loss |
|---|---|---|---|
| 13* | 188 | 185 | 2 |
| 14 | 192 | 30 | 84 |
| 15 | 154 | 5 | 97 |

Films 1–6, 7–10, and 11–15 represent the results for three separate experiments. Films 1–6 and 11–15 are shaken for 4 days while Films 7–10 are shaken for 5 days. The films with the * represent control films.

In every case, weight loss of 84–99% is observed for the inoculated films and only 0.6–6.4% for the control films. Cellulose Acetate, DS=2.5.

| Film Number | Original Weight (mg) | Final Weight (mg) | % Weight Loss |
|---|---|---|---|
| 1* | 135 | 136 | 0 |
| 2* | 161 | 161 | 0 |
| 3* | 132 | 131 | 0.8 |
| 4 | 147 | 148 | 0 |
| 5 | 146 | 40 | 73 |
| 6 | 169 | 60 | 65 |
| 7 | 175 | 81 | 54 |
| 8 | 157 | 36 | 77 |

Each film is shaken for 12 days. The films with the * represent control films. In every case, weight losses of 54–77% are observed for the inoculated films and 0–0.8% for the control films. As expected, the films with a higher degree of substitution exhibit greater resistance to microbial attack.

Figure 5:
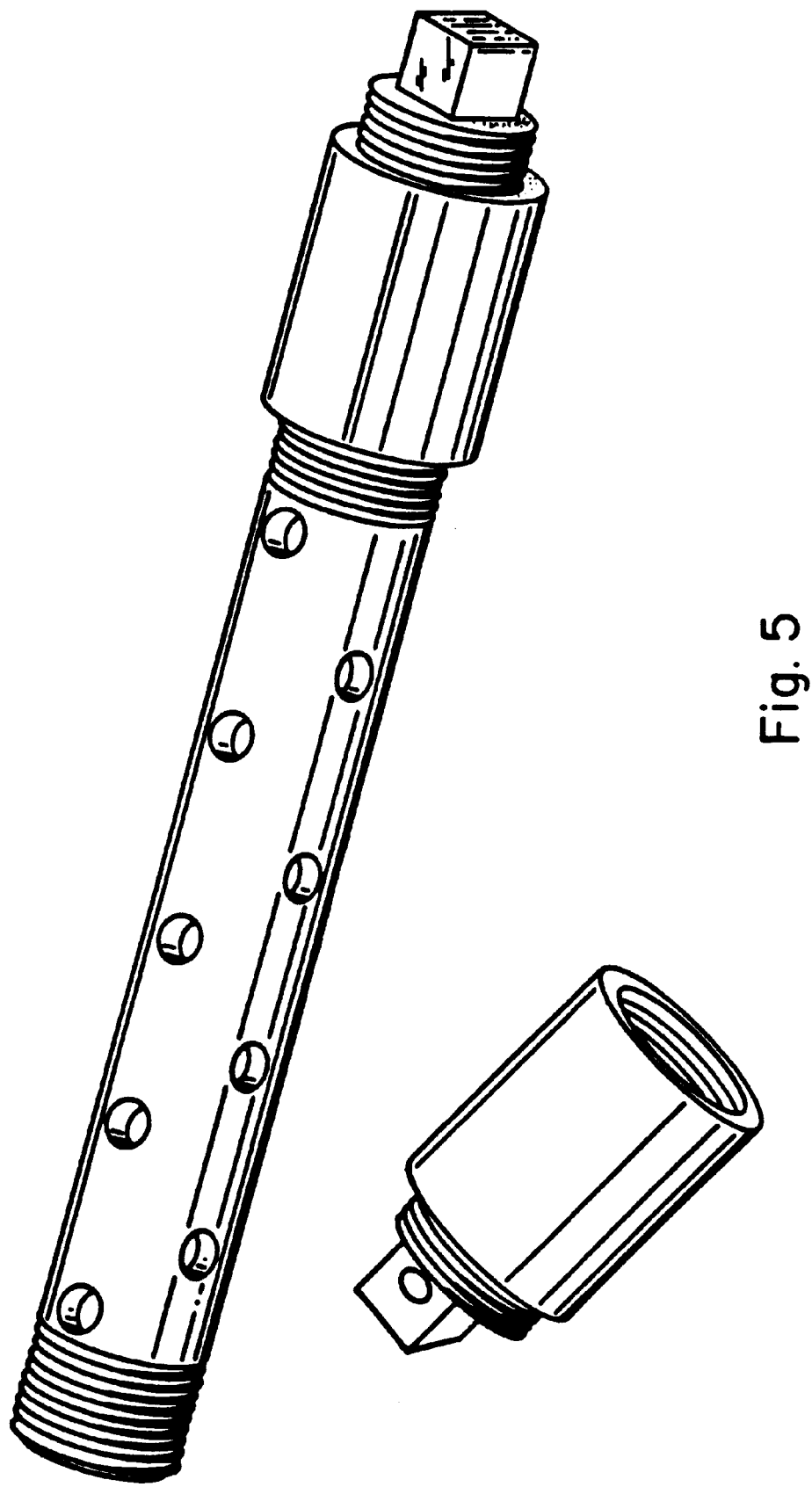
FIG. 5—The type of cylinder used for suspending film strips in wastewater basins. Strips of film 0.5 inch wide and 6 inches long of known weight and thickness were placed in the cylinder which was attached to a steel cable and immersed in a wastewater basin.

Wastewater Treatment Studies: Fifteen numbered cylinders, such as the one shown in FIG. 5, containing one cellulose acetate film each are attached to a steel cable and suspended in Tennessee Eastman's AD02 basin. Films 1–4 are harvested after 21 days while Films 5–14 are harvested after 27 days. The harvested films are suspended in a neutral detergent solution at 90° C. for 30–60 minutes before washing extensively with water. The films are placed in a vacuum oven at 40° C. until dry before weighing.

Cellulose Acetate, DS=1.7.

| | | Biodegradation of Cellulose Acetate (DS = 1.7) In Wastewater Treatment Plant | | | | |
|---|---|---|---|---|---|---|
| Film No. | Original Wt. (mg) | Final Wt. (mg) | % Wt. Loss | Original Thickness | Final Thickness | % Thickness Loss |
| 1 | 223 | 176 | 21 | 6.40 | 5.28 | 18 |
| 2 | 217 | 172 | 21 | 6.33 | 5.59 | 12 |
| 3 | 187 | 150 | 20 | 5.61 | 5.30 | 6 |
| 4 | 249 | 200 | 20 | 5.96 | 5.48 | 8 |
| 5 | 186 | 51 | 73 | 5.56 | 4.08 | 21 |
| 6 | 243 | 75 | 69 | 6.95 | 4.78 | 31 |
| 7 | 220 | 62 | 72 | 6.35 | — | — |
| 8 | 243 | 78 | 68 | 6.29 | 4.55 | 28 |
| 9 | 201 | 19 | 91 | 5.40 | 4.30 | 19 |
| 10 | 146 | 28 | 81 | 5.97 | 4.08 | 32 |
| 11 | 201 | 21 | 90 | 5.79 | 3.83 | 34 |
| 12 | 160 | 44 | 73 | 5.66 | 4.65 | 18 |
| 13 | 197 | 70 | 65 | 6.59 | 4.93 | 25 |
| 14 | 199 | 50 | 75 | 5.71 | 4.92 | 14 |

The films tested after 21 days show a weight loss of 20–21% while the films tested after 27 days show a weight loss of 65–91%. The large loss in film weight and thickness between days 21 and 27 is typical. Generally, an induction period is observed during which microbial attachment is occurring. When the bacteria are attached and enough degradation has occurred to expose more surface area, the rate of degradation increases. Films 2–4 are intact enough so that testing of mechanical properties and comparison to control films (A–C) is possible:

| Film Number | Tangent Modulus ($10^5$ psi) | Tensile Strength ($10^3$ psi) |
|---|---|---|
| 2 | 1.47 | 2.62 |
| 3 | 1.25 | 1.49 |
| 4 | 1.44 | 2.62 |
| A | 2.63 | 4.85 |
| B | 2.91 | 6.04 |
| C | 2.41 | 5.09 |

In each case, substantial loss in the tangent modulus and tensile strength is observed which illustrates how the microbial degradation of the test films leads to loss in film properties.

Compost Biodegradation Assays: Composting can be defined as the microbial catalyzed degradation and conversion of solid organic waste into soil. One of the key characteristics of compost piles is that they are self heating; heat is a natural by-product of the metabolic breakdown of organic matter. Depending upon the size of the pile, or its ability to insulate, the heat can be trapped and cause the internal temperature to rise.

Efficient degradation within compost piles relies upon a natural progression or succession of microbial populations to occur. Initially the microbial population of the compost is dominated by mesophilic species (optimal growth temperatures between 20–45° C.). The process begins with the proliferation of the indigenous mesophilic microflora and metabolism of the organic matter. This results in the production of large amounts of metabolic heat which raises the internal pile temperatures to approximately 55–65° C. The higher temperature acts as a selective pressure which favors the growth of thermophilic species on one hand (optimal growth range between 45–60° C.), while inhibiting the mesophiles on the other. Although the temperature profiles are often cyclic in nature, alternating between mesophilic and thermophilic populations, municipal compost facilities attempt to control their operational temperatures between 55–60° C. in order to obtain optimal degradation rates. Municipal compost units are also typically aerobic processes, which supply sufficient oxygen for the metabolic needs of the microorganisms permitting accelerated biodegradation rates.

In order to assess the biodegradation potential of the test films, small-scale compost units were employed to simulate the active treatment processes found in a municipal solid waste composter. These bench-scale units displayed the same key features that distinguish the large-scale municipal compost plants. The starting organic waste was formulated to be representative of that found in municipal solid waste streams: a carbon to nitrogen ratio of 25:1, a 55% moisture content, a neutral pH, a source of readily degradable organic carbon (e.g., cellulose, protein, simple carbohydrates, and lipids), and had a particle size that allowed good air flow through the mass. Prior to being placed in a compost unit, all test films were carefully dried and weighed. Test films were mixed with the compost at the start of an experiment and incubated with the compost for 10 to 15 days. The efficiency of the bench scale compost units was determined by monitoring the temperature profiles and dry weight disappearance of the compost. These bench scale units typically reached 60–65° C. within 8 hours. After 15 days of incubation there was typically a 40% dry weight loss in the compost. Films were harvested after 10 or 15 days of incubation and carefully washed, dried, and weighed to determine weight loss. The following is representative of the results of such composting experiments:

Composting Results: 15 Day Composting Trial

| Film Composition | Weight Loss | Film Thickness (mil) |
|---|---|---|
| 55/45 CAP (DS = 2.15)/PEG | 36% | 0.63 |
| 55/45 CAP (DS = 2.15)/PTG | 29% | 0.68 |
| 60/40 CAP (DS = 2.7)/PTG + 1% microcrystalline cellulose | 16% | 2.77 |
| 60/40 CAP (DS = 2.7)/PTG | 14% | 2.38 |

Composting Results: 10 Day Composting Trial

| Film Composition | Weight Loss | Film Thickness (mil) |
|---|---|---|
| 45/55 CAP (DS = 2.09)/PEG | 47% | 0.45 |
| 55/45 CAP (DS = 2.15)/PEG | 29% | 0.61 |
| 55/45 CAP (DS = 2.49)/PTG | 26% | 0.56 |
| 60/40 CAP (DS = 2.7)/PTG + 2.5% CaCO$_3$ | 22% | 0.98 |
| 60/40 CAP (DS = 2.7)/PTG + 2% cellulose monoacetate | 20% | 5.31 |
| PTG (T) [60/40] | 17% | 2.95 |
| PTG (T) (D) [60/35/5] | 16% | 19.2 |

The invention has been described in detail with particular reference to preferred embodiments thereof, but it will be understood that variations and modifications can be effected within the spirit and scope of the invention. Moreover, all patents, patent applications (published or unpublished, foreign or domestic), literature references or other publications noted above are incorporated herein by reference for any disclosure pertinent to the practice of this invention.

We claim:

1. A uniaxially or biaxially oriented plastic film comprising an essentially linear, random, semicrystalline aliphatic-aromatic copolyester which has an inherent viscosity of about 0.5 to 1.8 deciliters/gram as measured at a temperature of 25° C. for a 0.5 g sample in 100 mL of a 60/40 parts by weight solution of phenol/tetrachloroethane wherein the aliphatic-aromatic copolyester is comprised of repeat units of the following structure:

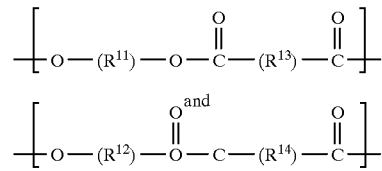

wherein $R^{11}$ and $R^{12}$ are the same and are selected from the groups consisting of $C_4$ and $C_6$ alkylene wherein $R^{11}$ and $R^{12}$ are 100% of the diol components; $R^{13}$ is selected from the group consisting of $C_3$–$C_4$ alkylene wherein the mole % of $R^{13}$ is from about 40–60% of the dicarboxylic components; and $R^{14}$ is selected from the group consisting of C6–C10 aryl wherein the mole % of $R^{14}$ is from about 60–40% of the dicarboxylic component.

* * * * *

UNITED STATES PATENT AND TRADEMARK OFFICE
Certificate

Patent No. 5,900,322                                                    Patented: May 4, 1999

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Charles M. Buchanan, Bluff City, Tennessee; Robert M. Gardner, Gray, Tennessee; and Alan W. White, Kingsport, Tennessee.

Signed and Sealed this Twenty-sixth Day of February 2002.

<div align="right">

VASUDEVAN S. JAGANNATHAN
*Supervisory Patent Examiner*
Art Unit 1714

</div>